United States Patent
Howard

(10) Patent No.: US 10,154,812 B2
(45) Date of Patent: *Dec. 18, 2018

(54) SYSTEM, METHOD, AND APPLICATIONS OF USING THE FUNDAMENTAL CODE UNIT AND BRAIN LANGUAGE

(71) Applicant: Newton Howard, Arlington, VA (US)

(72) Inventor: Newton Howard, Arlington, VA (US)

(73) Assignee: Newton Howard, Providence, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/219,255

(22) Filed: Jul. 25, 2016

(65) Prior Publication Data

US 2017/0164895 A1    Jun. 15, 2017

Related U.S. Application Data

(63) Continuation of application No. 13/747,448, filed on Jan. 22, 2013, now Pat. No. 9,399,144, which is a
(Continued)

(51) Int. Cl.
*A61N 1/00* (2006.01)
*A61B 5/00* (2006.01)
(Continued)

(52) U.S. Cl.
CPC .......... *A61B 5/4839* (2013.01); *A61B 5/0476* (2013.01); *A61B 5/112* (2013.01); *A61B 5/407* (2013.01); *A61B 5/4082* (2013.01); *A61B 5/4088* (2013.01); *A61B 5/4803* (2013.01); *A61B 5/4824* (2013.01); *A61M 21/02* (2013.01); *A61N 2/006* (2013.01); *A61N 5/0622* (2013.01);
(Continued)

(58) Field of Classification Search
USPC .................................................. 607/3, 7, 62
See application file for complete search history.

(56) References Cited

U.S. PATENT DOCUMENTS

| 6,159,015 A | 12/2000 | Buffington et al. |
| 6,338,628 B1 | 1/2002 | Smith |

(Continued)

OTHER PUBLICATIONS

Non-final Office Action dated Apr. 18, 2013 issued in U.S. Appl. No. 12/880,042.
(Continued)

*Primary Examiner* — Nicole F Johnson
(74) *Attorney, Agent, or Firm* — Smith, Gambrell & Russell, LLP

(57) ABSTRACT

The present invention relates to a non-invasive system with diagnostic and treatment capacities that use a unified code that is intrinsic to physiological brain function. In an embodiment of the present invention, an approach to the treatment of disorders that supplements existing diagnostic and treatment methods with robust quantitative data analysis are presented. This is achieved by a unification of cognitive and neural phenomena known as the Fundamental Code Unit (FCU), representing identifiable patterns of brain activity at the submolecular, molecular, and cellular levels (intrabrain communications), as well as their manifestations in thought and language (inter-brain communications).

20 Claims, 12 Drawing Sheets

Related U.S. Application Data continuation-in-part of application No. 13/083,352, filed on Apr. 8, 2011, now abandoned, and a continuation-in-part of application No. 12/880,042, filed on Sep. 10, 2010.

(60) Provisional application No. 61/588,666, filed on Jan. 20, 2012, provisional application No. 61/322,158, filed on Apr. 8, 2010, provisional application No. 61/241,314, filed on Sep. 10, 2009.

(51) Int. Cl.
  *A61N 2/00* (2006.01)
  *A61N 5/06* (2006.01)
  *A61M 21/02* (2006.01)
  *A61B 5/0476* (2006.01)
  *A61B 5/11* (2006.01)
  *A61N 5/10* (2006.01)
  *A61N 7/00* (2006.01)
  *A61M 21/00* (2006.01)

(52) U.S. Cl.
  CPC ............. *A61M 2021/0027* (2013.01); *A61M 2021/0044* (2013.01); *A61N 2005/1087* (2013.01); *A61N 2007/0026* (2013.01)

(56) References Cited

U.S. PATENT DOCUMENTS

| | | | |
|---|---|---|---|
| 7,648,498 | B2 | 1/2010 | Hempel |
| 2003/0040080 | A1* | 2/2003 | Miesenbock .... C07K 14/43581 435/69.1 |
| 2003/0195584 | A1 | 10/2003 | Dawson |
| 2004/0019370 | A1 | 1/2004 | Gliner et al. |
| 2004/0186719 | A1 | 9/2004 | Polanyi et al. |
| 2005/0118558 | A1 | 6/2005 | Wallis et al. |
| 2005/0142524 | A1 | 6/2005 | Simon et al. |
| 2005/0250082 | A1 | 11/2005 | Baldwin et al. |
| 2006/0004279 | A1* | 1/2006 | Ikeda ................... G06T 7/0012 600/411 |
| 2006/0095251 | A1 | 5/2006 | Shaw |
| 2007/0117073 | A1 | 5/2007 | Walker et al. |
| 2007/0225674 | A1 | 9/2007 | Molnar et al. |
| 2009/0157389 | A1 | 6/2009 | Shaw |
| 2011/0015538 | A1 | 1/2011 | Matthews, Jr. |
| 2011/0027765 | A1 | 2/2011 | Nader |
| 2012/0219934 | A1 | 8/2012 | Nakane et al. |

OTHER PUBLICATIONS

Response filed Oct. 18, 2013 in U.S. Appl. No. 12/880,042.
Final Office Action dated Jan. 30, 2014 issued in U.S. Appl. No. 12/880,042.
Amendment filed Jul. 30, 2014 in U.S. Appl. No. 12/880,042.
Non-final Office Action dated Sep. 10, 2014 issued in U.S. Appl. No. 12/880,042.
Amendment filed Feb. 10, 2015 in U.S. Appl. No. 12/880,042.
Final Office Action dated Jun. 4, 2015 issued in U.S. Appl. No. 12/880,042.
Amendment filed Dec. 3, 2015 in U.S. Appl. No. 12/880,042.
Non-final Office Action dated Jan. 15, 2016 issued in U.S. Appl. No. 12/880,042.
Amendment filed Jul. 15, 2016 in U.S. Appl. No. 12/880,042.
Final Office Action dated Nov. 1, 2016 issued in U.S. Appl. No. 12/880,042.
Amendment filed May 1, 2017 in U.S. Appl. No. 12/880,042.
Non-final Office Action dated Sep. 22, 2017 issued in U.S. Appl. No. 12/880,042.
Final Office Action dated Jul. 5, 2018 issued in U.S. Appl. No. 12/880,042.
Amendment filed Mar. 22, 2018 in U.S. Appl. No. 12/880,042.
Non-final Office Action dated Aug. 8, 2014 issued in U.S. Appl. No. 13/747,448.
Amendment filed Feb. 9, 2015 in U.S. Appl. No. 13/747,448.
Final Office Action dated Mar. 18, 2015 issued in U.S. Appl. No. 13/747,448.
Notice of Allowance dated Oct. 1, 2015 issued in U.S. Appl. No. 13/747,448.
Notice of Allowance dated Jan. 14, 2016 issued in U.S. Appl. No. 13/747,448.
Notice of Allowance dated May 11, 2016 issued in U.S. Appl. No. 13/747,448.
Non-final Office Action dated Feb. 27, 2013 issued in U.S. Appl. No. 13/083352.
Notice of Abandonment dated Sep. 10, 2013 issued in U.S. Appl. No. 13/083352.
Notification of Transmittal of International Search Report and the Written Opinion dated Jun. 21, 2011 received in International Application No. PCT/US2011/031819.
Notification Concerning Transmittal of International Preliminary Report on Patentability dated Oct. 18, 2012 received in International Application No. PCT/US2011/031819.
News Bias Explored; Word Choice Buffet: All You Can Eat. [Jun. 30, 2009], {Retrieved Feb. 19, 2013 U <http://www.umich.edu/-newsbias/wcact.html>, [Retrieved from Internet Archive Wayback Machine <URL: http://web.archive.org/web/20090630024420/http://www.umich.edu/-newsbias/wcact.html».
H.D. Block, The Perceptron: A Model for Brain Functioning. I*, Reviews of Modern Physics, vol. 34, No. 1 dated Jan. 1962 pp. 123-135.
Brian S. Blais, et al., the role of presynaptic activity in monocular deprivation: Comparison of homosynaptic and heterosynaptic mechanisms, Proc. Natl. Acad. Sci, USA, vol. 96, pp. 1083-1087, Feb. 1999.
Sydney Lamb- lamb@rice.edu, Wenzao Ursuline College of Languages, Kaohsiung, Taiwan, on the Neurocognitive Basis of Language, pp. 1-156, Nov. 12, 2010.
Simon B. Laughlin and Terrence J. Sejnowski, HHMI Howard Hughes Medical Institute, Published as: Science. Sep. 26, 2003; 301 (6541): pp. 1870-1874.
Brian Blais, Leon N. Cooper, Harel Shouval, Formation of Direction Selectivity in Natural Scene Environments, Neural Computation, vol. 12, Issue 5, pp. 1057-1066, May 2000.
Allen Institute for Brain Science, www.alleninstitute.org, captured Jan. 6, 2009 by Internet Archive Wayback Machine.
New Atlas Resource and Enhances Others With New Data and Tools, Nov. 14, 2008, from http://alleninstitute.org/content/Press/2008_1114_PressRelease_DataRelease.pdf.
Amendment filed Sep. 17, 2015 in U.S. Appl. No. 13/747,448.

* cited by examiner

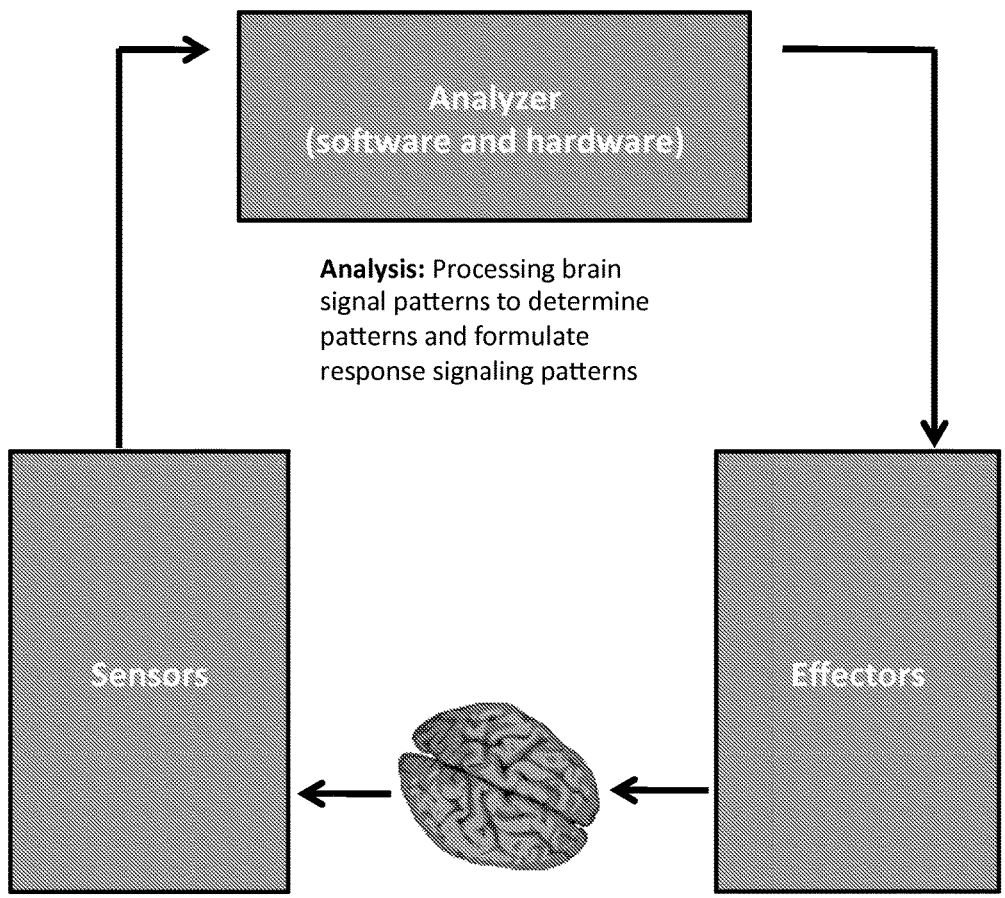
Figure 1: High level overview of the system

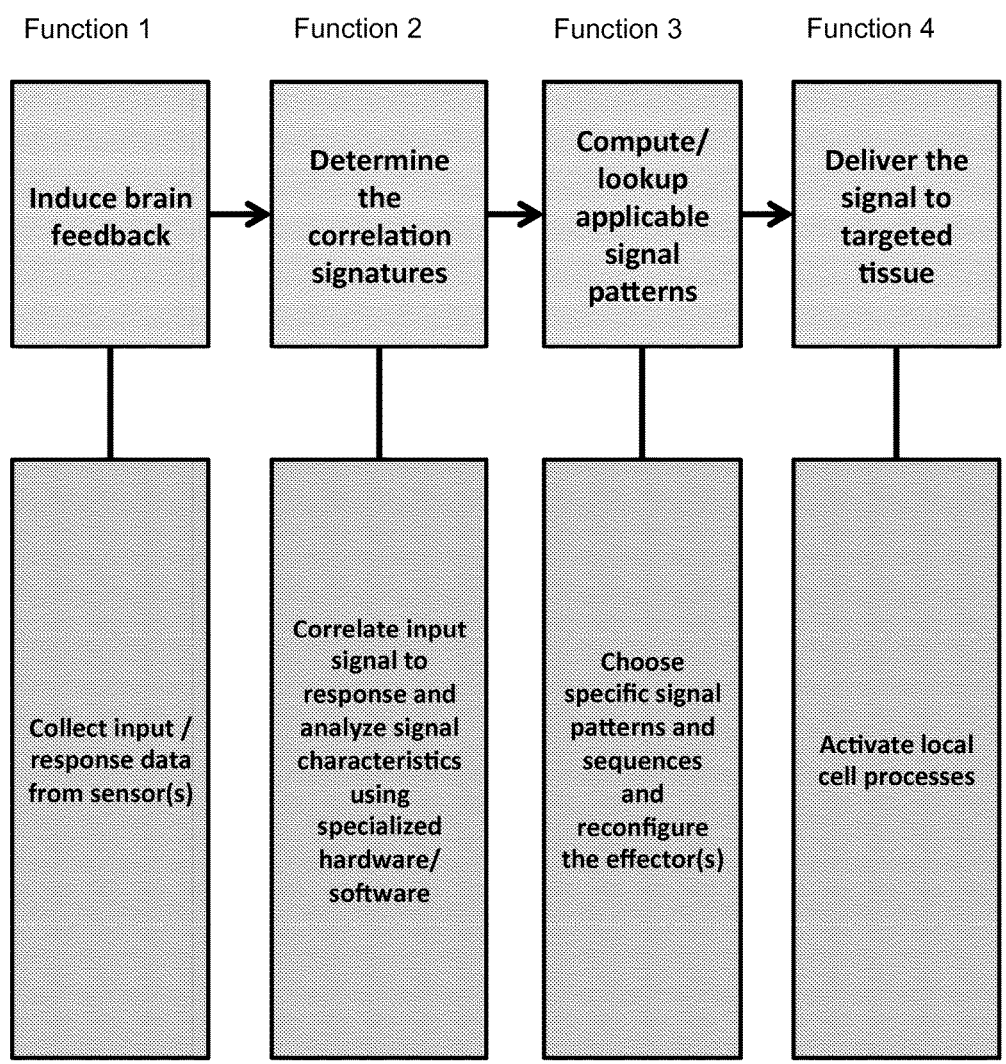
Figure 2: Sequence of steps

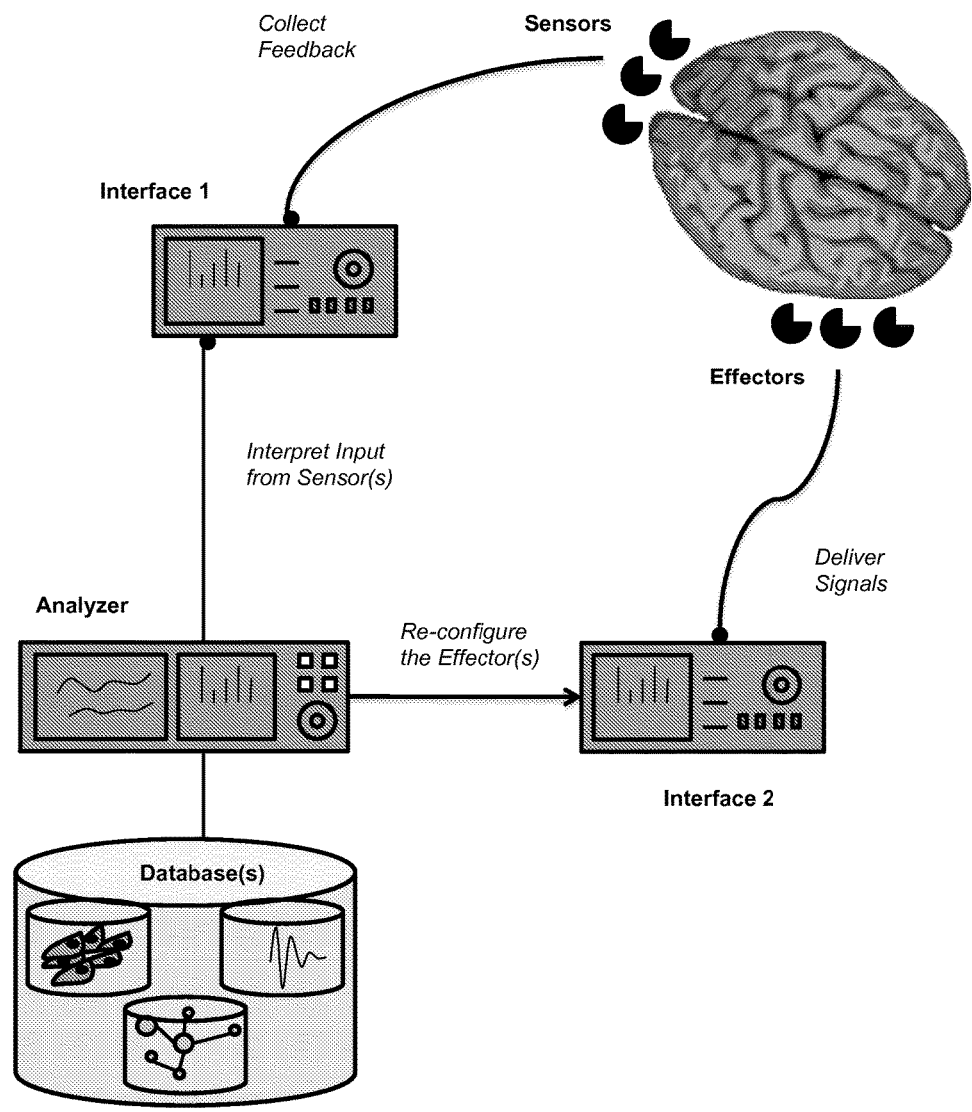
Figure 3: Example embodiment

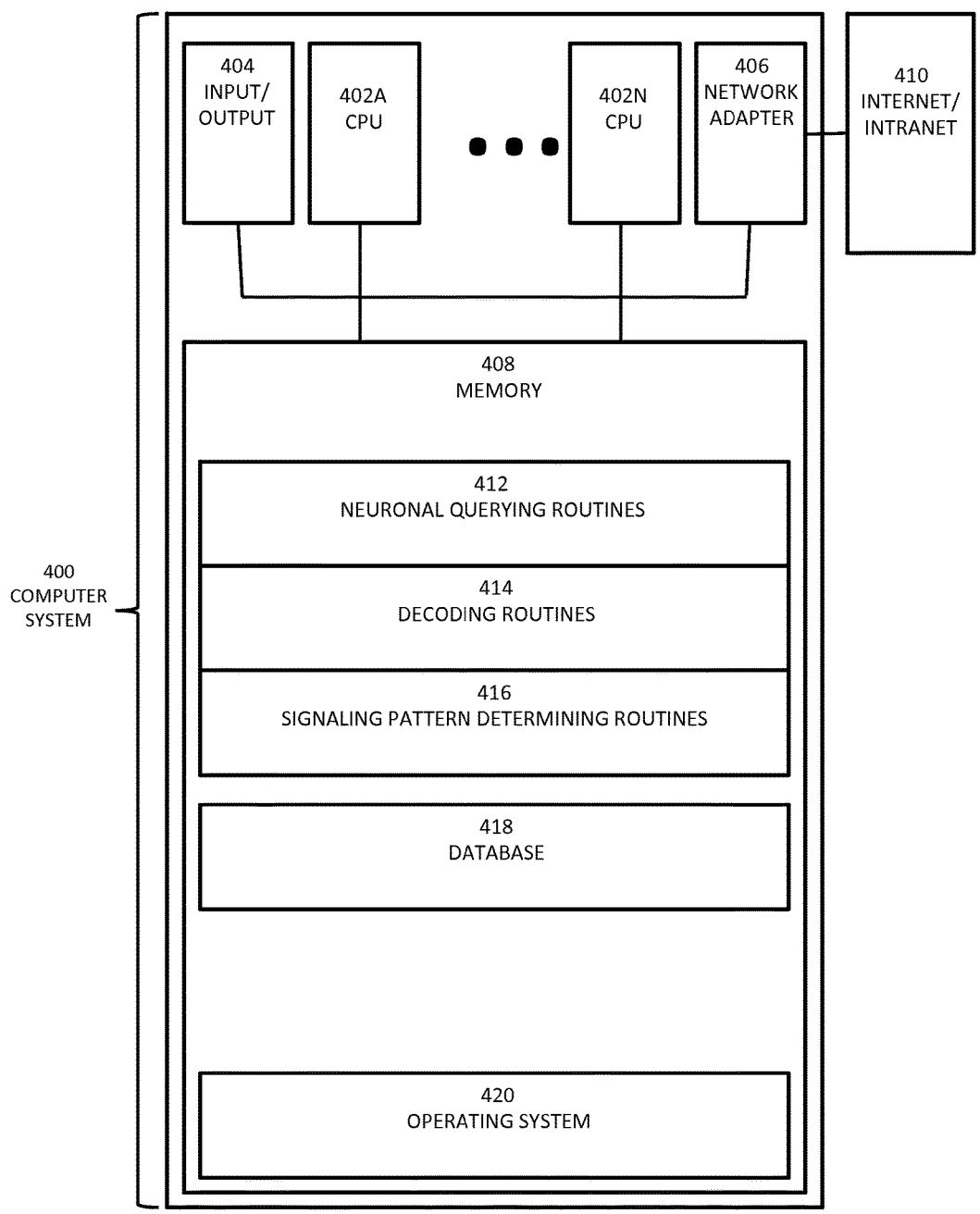
Figure 4: Hardware implementation

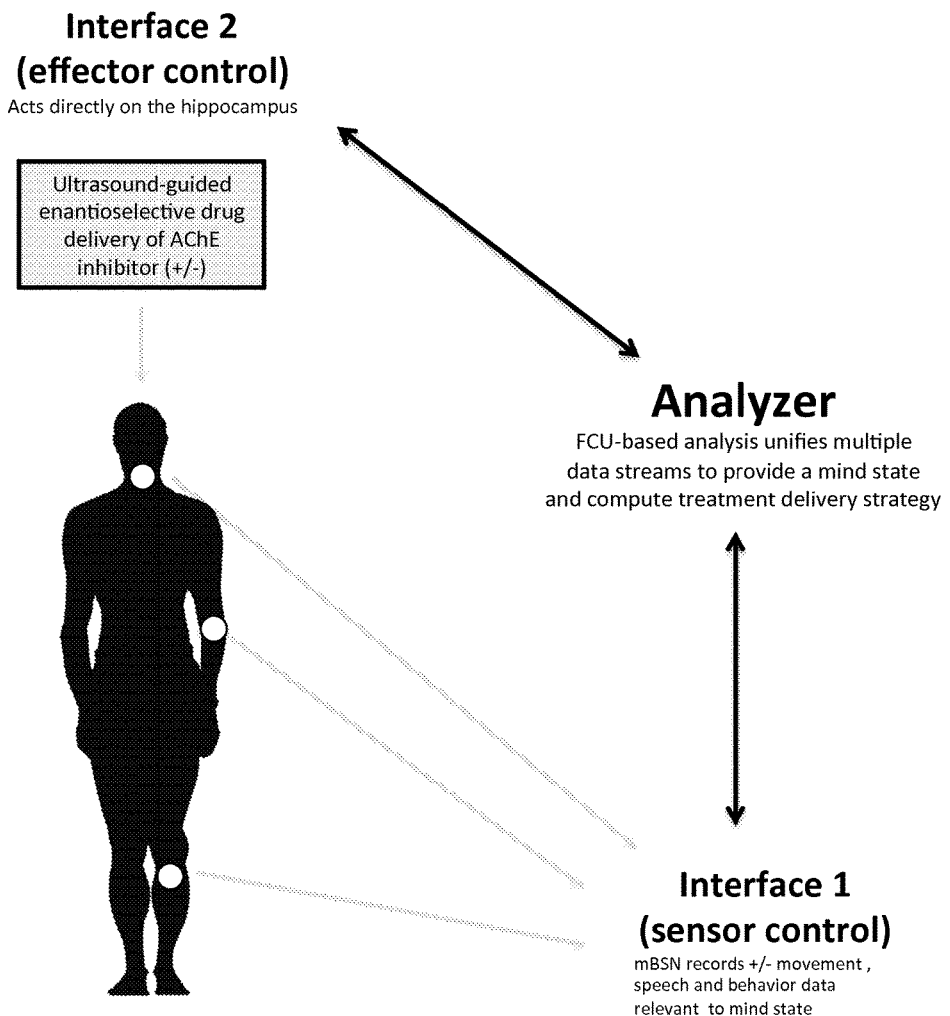
Figure 5: Example embodiment (additional details)

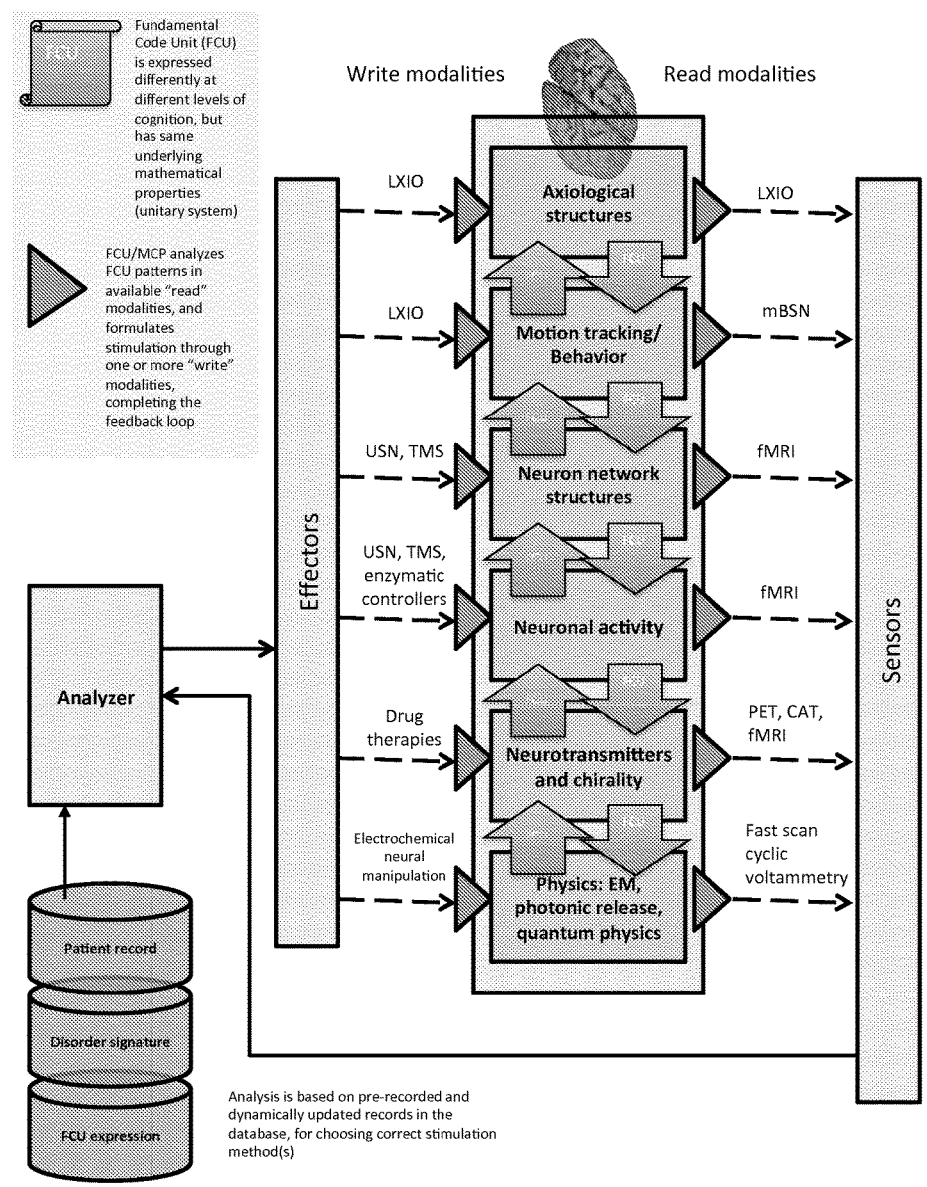
Figure 6: FCU/MCP multi-level analysis and example read & write modalities

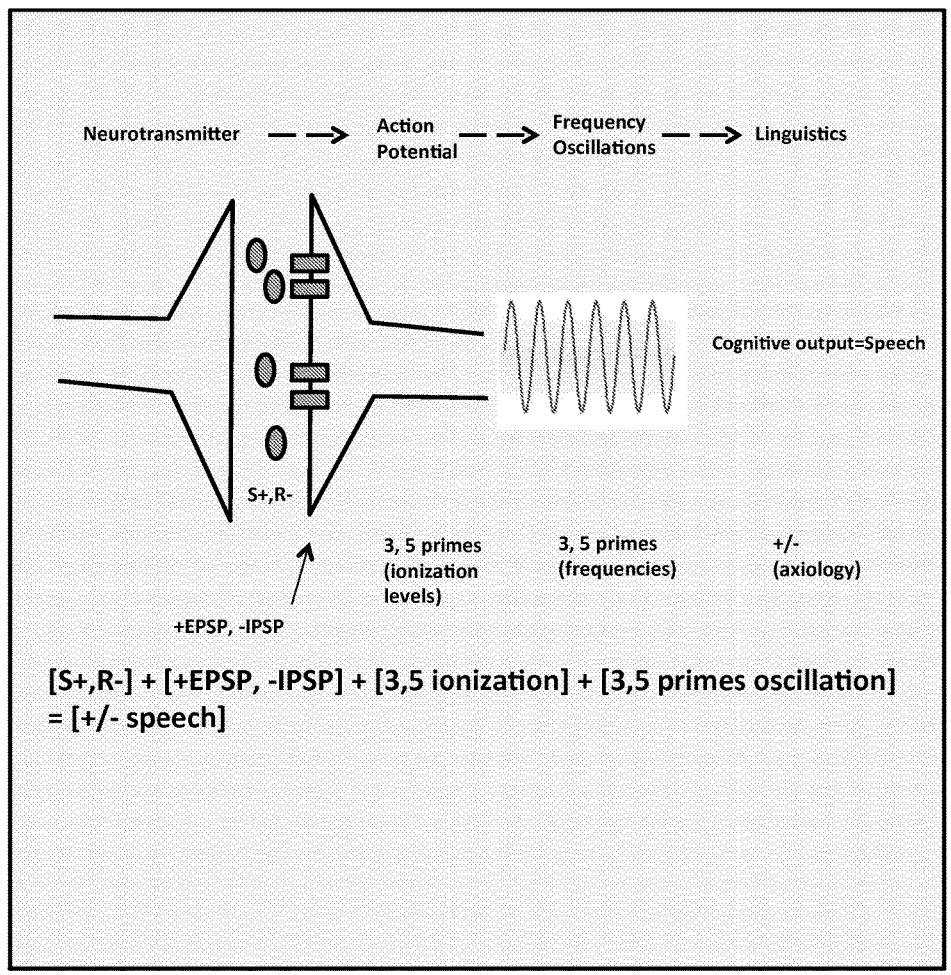
Figure 7: Multi-level code translation from neuronal interaction to cognition and language

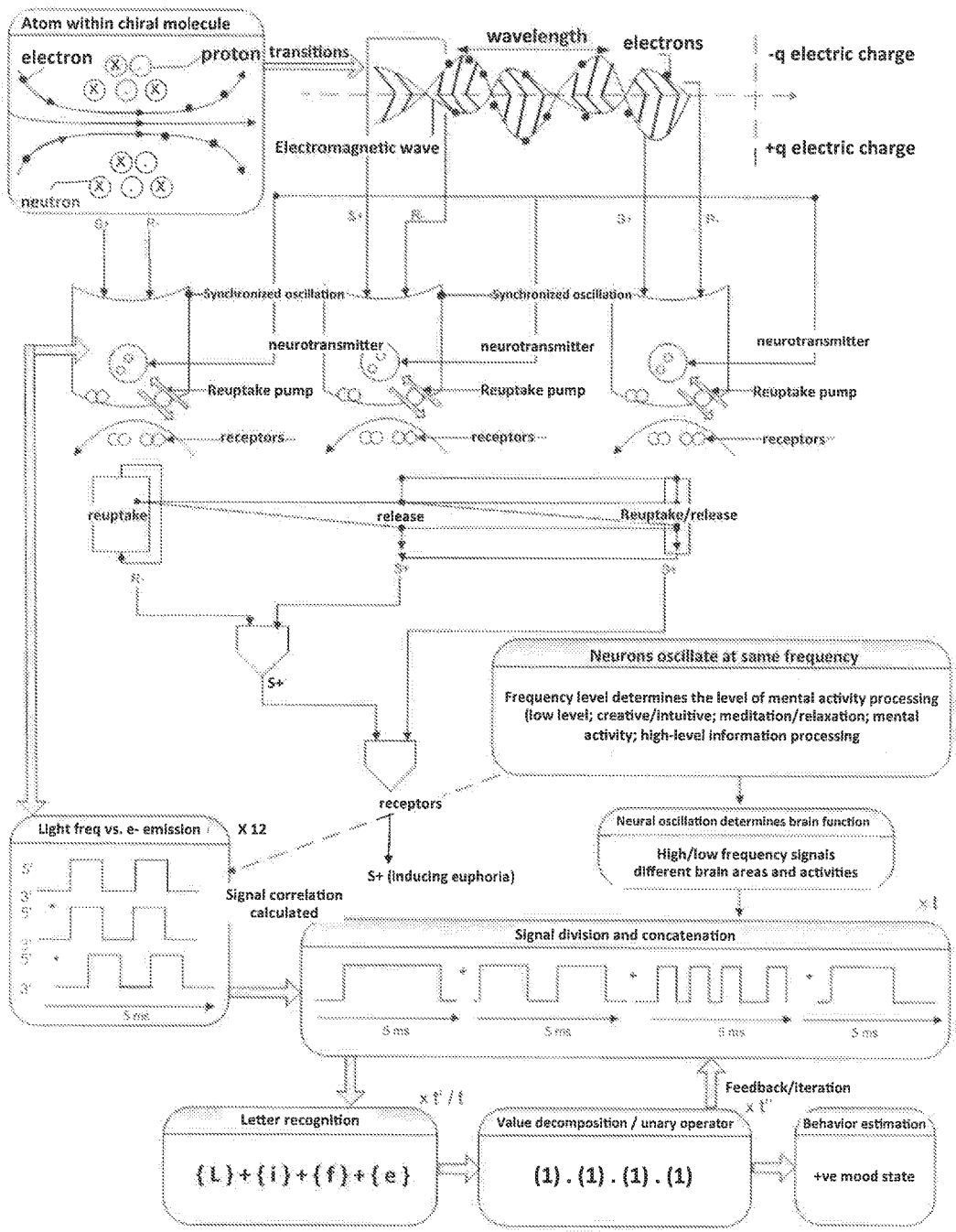

Figure 9: Autofluorescence
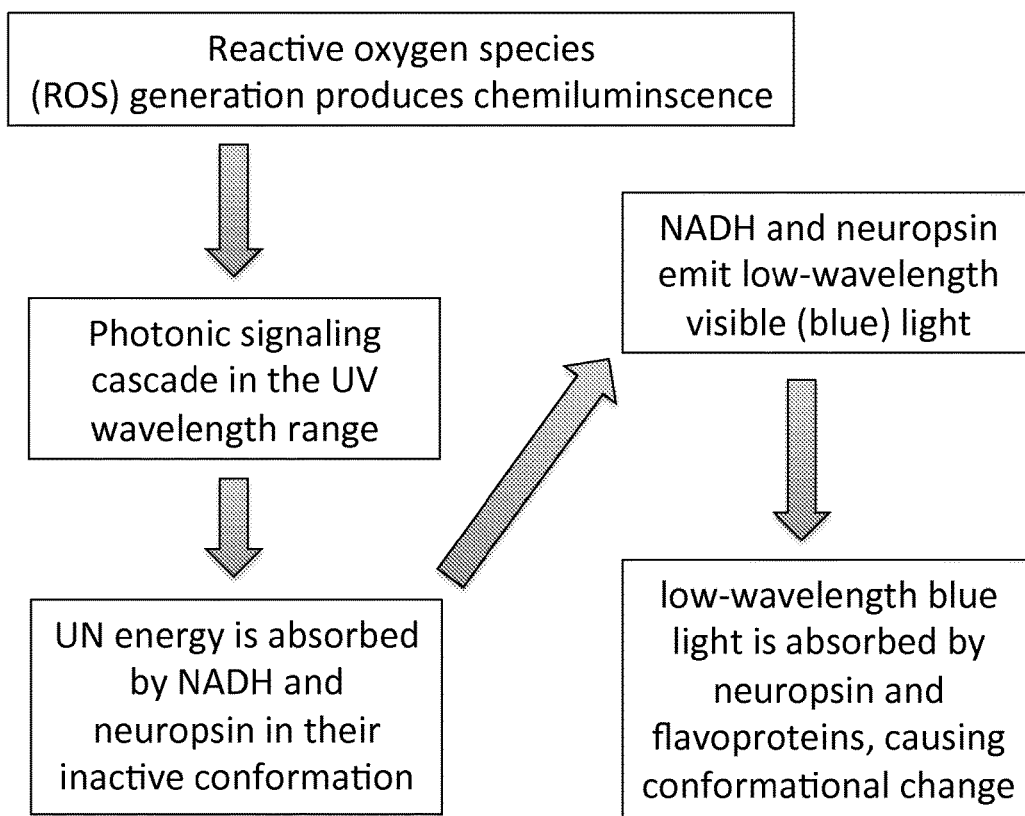

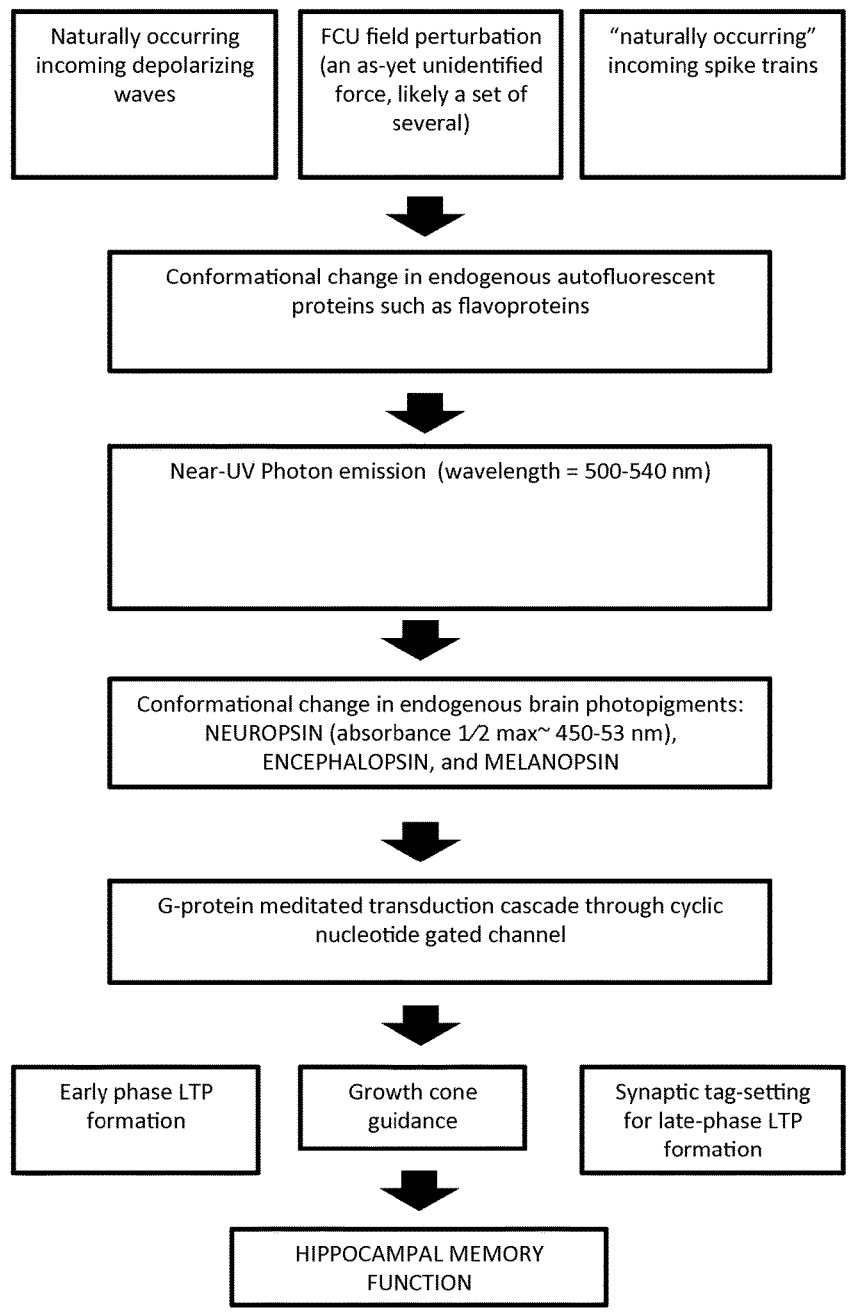
Figure 10: A proposed FCU-based mechanism for exchanging information within the brain: endogenous photon-triggered neuropsin transduction

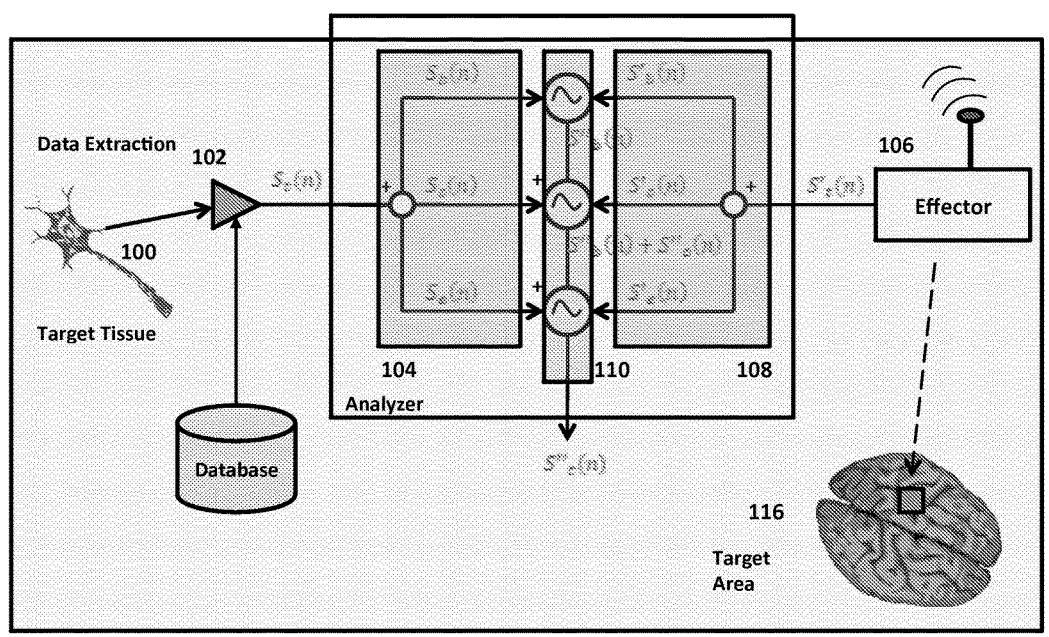
Figure 11: Detailed input and output

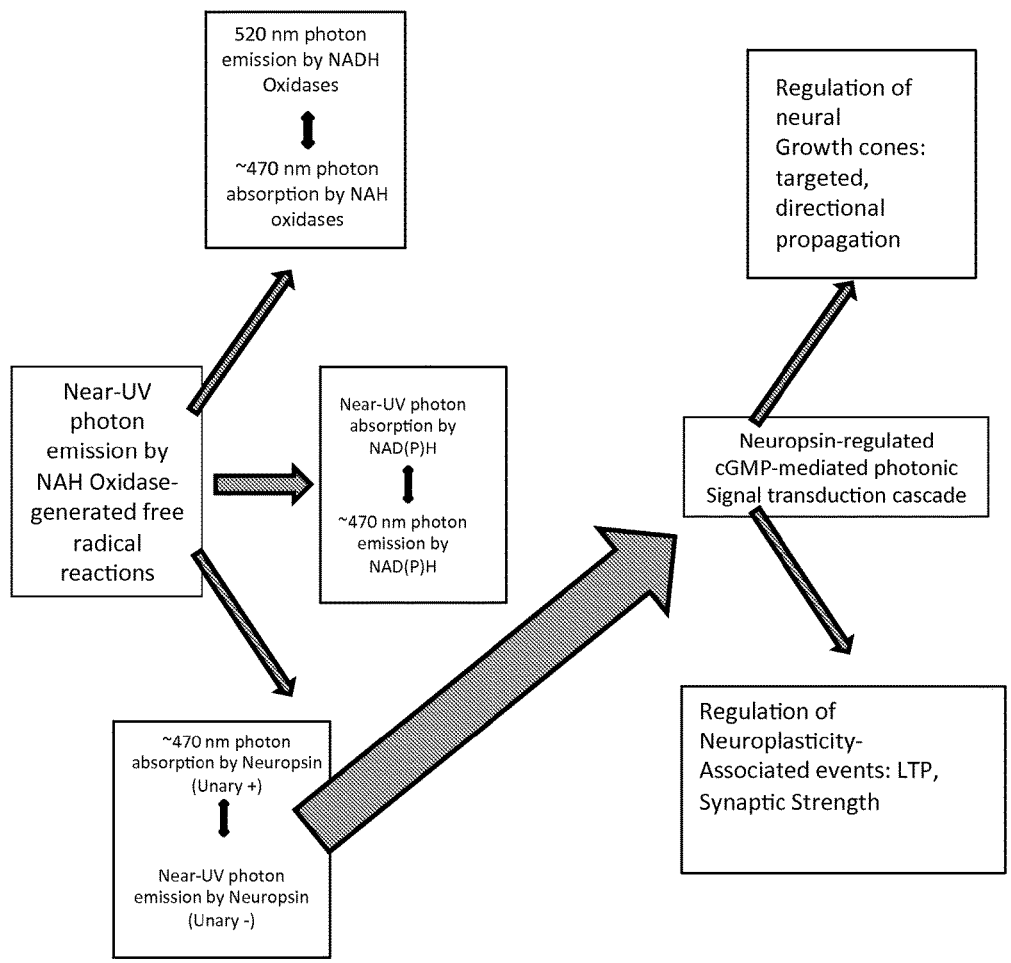
Figure 12: Photonic neural coding scheme

SYSTEM, METHOD, AND APPLICATIONS OF USING THE FUNDAMENTAL CODE UNIT AND BRAIN LANGUAGE

CROSS-REFERENCE TO RELATED APPLICATIONS

This application claims the benefit of Provisional Application No. 61/588,666, filed Jan. 20, 2012, the contents of which are incorporated herein in their entirety. This application is a continuation of U.S. patent application Ser. No. 13/747,448, filed Jan. 22, 2014, now patented as U.S. Pat. No. 9,399,144, issued Jul. 26, 2016, which is a continuation-in-part of U.S. patent application Ser. No. 13/083,352, filed Apr. 8, 2011, published as U.S. Patent Publication No. 2012-0064493 A1 on Mar. 15, 2012, now abandoned, which claims the benefit of U.S. Provisional Application No. 61/322,158, filed Apr. 8, 2010, the contents of both of which are incorporated herein in their entirety. This application is a continuation-in-part of U.S. patent application Ser. No. 12/880,042, filed Sep. 10, 2010, published as U.S. Patent Publication No. 2011-0060377 A1 on Mar. 10, 2011, which claims the benefit of U.S. Provisional Application No. 61/241,314, filed Sep. 10, 2009, the contents of both of which are incorporated herein in their entirety.

BACKGROUND OF THE INVENTION

Field of the Invention

The present invention relates to devices, methods and systems for detecting disorders of, and positively affecting the functioning of living tissues such as the brain and spinal cord.

Description of the Related Art

The successful development of new clinical concepts and interventions for neurological diseases of the brain require, first and foremost, a strong theoretical framework for understanding healthy brain function and the brain's capacity for intelligent action. Unfortunately, attempts to understand and explain brain function and dysfunction have been fragmented into several narrow fields of study. In order to study brain function, some researchers (for example, see www.alleninstitute.org) have attempted to reverse-engineer neuronal networks and even the brain itself. This approach was based on the assumption that neurons in-vivo acted just like simple transistors in-silico. Unfortunately, both network and whole-brain modeling have led to very little insight into actual brain function. This is largely because transistor based computing reacts to static events whilst neurons can react to processes. In contrast to transistors, neurons can establish and change their connections and vary their signaling properties according to a variety of rules, allowing them to adapt to circumstances, self-assemble, auto-calibrate and store information by changing their properties according to experience (Laughlin & Sejnowski, 2003). Consequently, a detailed understanding of neuronal function and network organization is required prior to neuronal network modeling attempts.

Block (1962) describes the "perceptron," or a series of sensory and associator units connected to resemble sensory and analytical components into a machine that vaguely models human response to sensory stimuli. Stimuli of a certain threshold trigger activity in specific associator units, which then activate those to which they are directly connected. Thus, different types of stimuli activate different networks of associator components. In this sense, Block's perceptron approach to modeling brain function privileges the connections between components rather than the components themselves as the primarily important in decoding human thought (Block 1962). However, there still remains the question of what constitutes a basic unit of connectivity. Does a single connection between two associates constitute a fundamental unit of perceptron "thought?" Studying the structure and function of different types of neural connections promises significant contributions, but this still doesn't answer the question of whether these connections consist of a "thought".

Lamb (2010) introduces the concept of the functional web, in which he posits that cognitive concepts such as single words and ideas (analogous to semantic primitives) are in fact spatially distributed across parts of the brain such as the cerebral cortex. Lamb splits these concepts into conceptual, motor, phonological image, tactile, and visual components, or components that roughly align with the senses. This approach not only applies to cognition but also to the concepts that comprise it, is intuitive since its criteria are empirically grounded. In addition, it unifies behavioral and linguistic with neurological activity. Lamb's approach is more focused on response and activation, but the nature of cognition is such that thought can beget more thought; an external agent is not consistently necessary. Tying cognition not just to specific sensory activity but also to brain activity in itself is also a requirement for successful modeling.

Blais et al. (2000) argue that modeling cognitive activity based on synaptic modification depends in large part on how synapses are stabilized after firing. With respect to synaptic activity, there are numerous types of "learning," each of which has a different neuronal effect. Hebbian learning, for instance, occurs when the connectivity between two neurons increases after one produces an action potential in the other. The selectivity-learning rule, on the other hand, incorporates a variable threshold of activation because it modulates the type and level of response to sensory stimuli (for instance, the difference between looking at the sun or at the night sky).

Blais et al. demonstrate an important mathematical connection between biology and temporality, or the idea that modeling such processes as cognition involves the accounting for change rather than for absolute physical values, and in doing so demonstrates the process parallelism that pervades natural phenomena.

There is a need for a new class of brain diagnostics and therapeutic devices. There is a need to unify the "read" and "write" aspects of clinical neuroscience. There is a need for detecting disorders of and positively affecting the functioning of living tissues such as the brain and spinal cord.

SUMMARY OF THE INVENTION

The present invention relates to a non-invasive system with diagnostic and treatment capacities that use a unified code that is intrinsic to physiological brain function. In an embodiment of the present invention, an approach to the treatment of disorders that supplements existing diagnostic and treatment methods with robust quantitative data analysis are presented. This is achieved by a unification of cognitive and neural phenomena known as the Fundamental Code Unit (FCU), representing identifiable patterns of brain activity at the submolecular, molecular, and cellular levels (intra-brain communications), as well as their manifestations in thought and language (inter-brain communications). In an embodiment of the present invention, a Medical Co-Processor (MCP) device correlates multiple data streams temporally using one or more read modalities, determines the patterns which are deleterious or sub-optimal, and uses a set of write modalities, or means to modify cognitive activity, to neutralize the negative effects of these patterns and stimulate patterns of activity which will have positive short- and long-term effects.

In an embodiment of the present invention, the methods by which the desired effects are achieved vary according to, but not limited to, the type and severity of the disorder. The method includes, but not limited to, querying the brain/spinal cord at multiple levels (individual neurons, neural networks, or entire brain areas), followed by decoding the responses, identifying and decoding signaling patterns, selecting treatment strategies, and applying them to induce specific cell behaviors for treating brain disorders in affected patients, and augmenting brain function in healthy subjects. In an embodiment of the present invention, the brain is queried invasively or non-invasively.

In an embodiment of the present invention acts as a Medical Co-Processor (MCP) device which, using a variety of sensors (which implement read modalities) and effectors (which implement write modalities), analyzes the response signals and provides series of signals to the brain or spinal cord and using analytical methods based on the Fundamental Code Unit (FCU), thereby decoding and treating the patient-, tissue- and disorder-specific signal patterns. The FCU/MCP device then uses pre-determined or dynamically determined signatures to select treatment frequencies and sends signals to the targeted tissue via a variety of methods (write modalities) using effector devices to stimulate the cells for specific protein switching/folding or electrochemical signaling sequences. The device therefore can be used for brain disorder diagnostics, and development of targeted treatment methods which activates the cells' internal resources.

In an embodiment of the invention, FCU/MCP uses both information representing both intra-cerebral activity (such as electrochemical patterns) and inter-cerebral activity (such as language and behavior), spanning the entire spectrum of invasive and noninvasive read and write modalities, including, but not limited to functional magnetic resonance imaging (fMRI), electroencephalography (EEG), neurotransmitter level and chirality measurement, linguistic analysis, ultrasound, transcranial magnetic stimulation (TMS), deep brain stimulation (DBS), audiovisual stimulation (AV), and others.

In an embodiment of the invention, read modality input is received via one or more sensor devices, which may range in complexity and functions, from vestibular sensors to voice input analyzers. The input is processed by the Analyzer, which applies multiple analytical methods to determine FCU patterns, performs lookups in one or more databases, and records newly identified patterns. The data are then inputted into computational algorithms based on FCU models and used to compute corrections to the defective neural functions. These computed corrections are used to feed back into the brain as perturbations of neural activity serving as treatment of injury/disorder utilizing Effector devices which implement write modalities to deliver signals to the brain.

BRIEF DESCRIPTION OF THE DRAWINGS

FIG. 1 is a high-level representation of FCU/MCP device determining specific FCU signal patterns and producing signals affecting cell functioning by invasive and non-invasive stimulation. This illustration is primarily concerned with the relationship between the read modality and write modality.

FIG. 2 is a high-level representation of coprocessor functions for implementing the manipulation of cellular structures via signaling, as outlined in FIG. 1. Signaling includes the controlled release of S (+) and R (−) isomer/enantiomer combinations to specific brain regions and neural networks. FIG. 2 serves to distinguish the chemical action of the FCU/MCP versus the blanket pharmaceutical interventions currently available.

FIG. 3 is an example of an apparatus implementing the invention, demonstrating the interconnections and functions of its composite parts. This includes both the read (input) and write (output) components of FCU/MCP.

FIG. 4 is a hardware implementation of the read and write modality hierarchy that illustrates the interaction between the coprocessor itself and its many sources of input. FIG. 4 also includes the database of existing patterns, querying routines, pattern analysis routines, and finally, input from the physiological system being analyzed.

FIG. 5 is an illustration of the read/write modality usage in the detection and treatment of a neurological disorder, Alzheimer's disease. The read modality, multimodal body sensor networks (mBSN), gathers data from presumptive Alzheimer's patient: movement/gait information from arms and legs and cognitive information from audio speech sensors. This information is sent to the Analyzer, through Interface 1, a Sensor control. The Analyzer computes unary mathematics (+/−) of the incoming motion and speech information and also computes unary delivery (S+/R−) of write modalities for treatment of Alzheimer's disease. Through Interface 2, the Analyzer configures an ultrasound Effector, which creates an ultrasonic beam that temporarily permits a narrow opening of the blood brain barrier to enable delivery of enantioselective acetylcholine esterase inhibitors (AChE). AChE is delivered directly to the hippocampus to treat Alzheimer's disease.

FIG. 6 provides a higher-level view of the relationship between sensors, or read modality elements, and effectors, or write modality elements. Each of these exists in a cyclic relationship with the next. The dual process of querying by read modalities and application of write modalities varied by type, duration and intensity is computed by unary mathematics of FCU and is used to diagnose and treat complex neurological disorders.

FIG. 7 illustrates the translation of neural code, from neurotransmitter and spike/pulse sequences, to action potentials, to frequency oscillations, and finally to cognitive output including speech and behavior. Original neural encoded information might be meaningful however, the meaning is not dependent on the interpretation. In neurological disorders, post-synaptic neurons may not be able to interpret and act on meaningful encoded messages that are transmitted to it.

FIG. 8 is a detailed schematic of the multiple levels at which the FCU analyzer operates, ranging from the sub-atomic (charged particle) level to the molecular neurotransmitter and finally the linguistic level.

FIG. 9 is a flow diagram of the process of autofluorescence.

FIG. 10 is a flow diagram of a proposed FCU-based mechanism for exchanging information within the brain: endogenous photon-triggered neuropsin transduction.

FIG. 11 is an example of an apparatus implementing the invention, demonstrating the interconnections and functions of its composite parts. This includes both the read (input) and write (output) components of FCU/MCP.

FIG. 12 illustrates photonic transduction in NAH Oxidase (NOX) and NAD(P)H. Both of these molecules are affected by light, and the emission of near-UV electromagnetic energy by NOX causes a similar reaction in neuropsin, whose emitted light wavelength can be used to interpret brain activity. What results is a neuropsin-regulated signaling transduction cascade, since the photon energy emitted by NOX is higher than the threshold required to change neuropsin's conformality.

DETAILED DESCRIPTION OF THE INVENTION

Device Description

The present invention acts as a Medical Co-Processor (MCP) device which, using a variety of brain stimulation methods and sensors (read modalities), such as deep brain stimulation (DBS), electroencephalography (EEG) or ultrasound, provides series of signals to the brain or spinal cord and analyzes the response signals using analytical methods based on the Fundamental Code Unit (FCU), thereby decoding the patient, tissue and disorder-specific signal patterns. The FCU/MCP device then uses pre-determined or dynamically determined signatures to select treatment frequencies and sends signals to the targeted tissue via a variety of methods (write modalities) using effector devices such as enzymic controllers, optogenetic interfaces, or other signal carrier techniques to stimulate the cells for neural plasticity changes, specific protein switching/folding or electrochemical signaling sequences. The device therefore can be used for brain disorder diagnostics, and development of targeted treatment methods which activate the cells' internal resources.

Fundamental Code Unit and the Unitary System

In an embodiment of the present invention, the Fundamental Code Unit (FCU), developed by Newton Howard (2012), is based on a mathematical construct known as the unitary system. Based on unary mathematics, this unitary system is clearly manifest in a number of physiological processes, including brain function and neuronal activity, molecular chirality and frequency oscillations within the brain. The unitary system is essentially a mechanism of spatiotemporal representation with a two-value (+ "plus" or − "minus") numerical system. At a synapse for instance, a neuron can release neurotransmitters that excite or inhibit another cell. The spectrum between these two poles, which is governed by the relative concentrations of each neurotransmitter, can be modeled according to these values since they bound the universe of discourse in this case. This system is used to represent many of the phenomena under the analytical purview of the Fundamental Code Unit, ranging from synapse activation and inactivation, to sensations of pain, to mind state calculations based on linguistic output.

Neural circuit perturbation can result from molecular as well as electromagnetic effects, causing changes in basal operation properties of local or global brain dynamics. Thus, interpreting the outcome of a causal neural circuit experiment included, but is not limited to, in the short term, the design of powerful control experiments, and in the longer term, radically better scaled methods for observing and influencing activity across the brain in order to understand the net neural impact of a perturbation.

One example application of the unitary system is in the detection of peripheral nerve injury, which is a common cause of neuropathic pain. The presence of such pain suggests that the dynamic mapping of neural inputs and outputs has been altered. Using the unitary system, we can measure the aggregate of altered +/− inputs from healthy synapses. One of the areas of the brain implicated in pain perception, the Anterior Cingulate Cortex (ACC), consists of both inhibitory (−) and excitatory (+) neurons that respond to pain stimuli (tissue damage, temperature variations, etc.) in opposite manners. Inhibitory neurons cause action potentials to fire less, while excitatory neurons cause them to fire more. Persistent changes in synaptic strength such as long-term potentiation is observed in ACC synapses and in response to noxious stimuli, there is enhanced glutamate release and increase in AMPA receptor expression postsynaptically. This suggests that aggregates of inhibitions and excitations might be altered, thus modulating the unitary system due to synaptic strength changes.

Multi-Level/Multi-Modal Approach

The FCU/MCP's is a multi-level structure. In an embodiment of the present invention, there are two fundamental categories of data streams to which we can access the unitary FCU value sequences, and later, to which we can assign diagnostic and clinical regimes. The first relates to activity within the brain (intracerebral). In an embodiment of the present invention, this includes, but is not limited to, molecular signaling via chiral and protein-based neurotransmitters, as well as hormonal signaling and amine and peptide-based chemical signaling mechanisms. In an embodiment of the present invention, the intracerebral level of analysis includes, but is not limited to, sub-molecular activity such as the production of specific synaptic proteins, such as neuropsin, resulting from increased electromagnetic activity (in the case of neuropsin, near-UV radiation in the 400-600 nm wavelength range). Finally, this layer includes connections between specific neurons and networks of neurons that may influence the manner in which specific cognitive events are manifested, such as memories (or lack thereof, as is the case in some forms of dementia).

The second relates to activity outside the brain, intracerebral activities are manifested behaviorally and linguistically. While these manifestations may appear to differ along cultural and geographical lines, the underlying neural processes driving them are identical, so they share the same underlying neural structure if not the same form. In terms of the FCU/MCP, behavior encompasses both voluntary and involuntary acts, since neurodegenerative diseases such as Parkinson's disease and Alzheimer's disease invoke uncontrollable behavioral changes. In addition to behavior, the extracerebral scope of FCU/MCP includes linguistic output as a means to determine mind state as well as cognitive faculty. In sum, the extracerebral realm of FCU/MCP is largely one of analysis and feedback, and the intracerebral component is an amalgam of analysis and clinical intervention. The primary distinguishing factor of FCU/MCP is thus the precise and holistic nature of the neural interventions and manipulations that take place. The importance of creating conceptual categories for each component of cognition relevant to FCU/MCP is that treatment modalities are created and employed in a manner that emulates these processes, rather than manipulates them using foreign chemical and electrophysical interventions.

Read modalities include a variety of ways in which a device can detect sequences of FCU values, and determine, for example, the potential effects of opening ion channels within the brain, as well as the expected changes to the conductance of these ions and protons beyond the immediate activation or silencing of cell. For instance, this might include, but is not limited to, the following:

long-term changes in neurons' storage of intracellular calcium changes in the pH of neural nuclei in the brainstem synaptically evoked neural spiking after photoactivation of neural ion pumps rebound effects within neurons silenced by GABA(A) receptor inhibitors Examining such less-studied effects such as these through the lens of novel read modalities helps lay conceptual groundwork for the second component of the FCU/MCP system: the write modality. FCU/MCP's write modality component includes both locally and remotely acting phenomena. In an embodiment of the invention, regarding local phenomena, optogenetic or pharmaceutical agents can be used to excite or inhibit specific neuron populations. Interventions, such as inhibitors and light-response treatment, promise to be significantly more effective at localized brain regions if the proper regions and cell networks can be identified. Neural modulators have a similar effect on neural network circuits, which means that the precise identification of vector networks for treatment delivery will likely be a significant component of future clinical neurology, with FCU/MCP taking the first steps toward that reality.

Stimulation or inhibition of brain activity using these methods essentially replicates what already happens to the brain in its natural form, but combined with read modalities, these methods will offer researchers and clinicians alike a uniquely precise methodology for targeting brain disorders. Studying potential downstream effects of specific types of brain activity and inactivity falls under the purview of the read modalities, and applying these methods to beneficially modifying brain processes is part of the write modalities.

Thus, for its read modality component, the FCU/MCP process flow is as follows: external observation→data acquisition→incorporation into FCU template→comparative analysis with other FCU templates at different levels of analysis→probabilistic diagnosis. Another key component of the system is the ability to use the FCU to compare an incomplete diagnostic picture (i.e., limited to a few external data streams) to previously collected data, including both healthy controls and patients with diagnosed disorders. This process promises to quicken the detection and identification of neurodegenerative disorders by reducing the amount and scope of data needed to make an authoritative diagnosis, as well as providing better access to existing information.

We expect the future of MCP research and applications to unfold in a rapid progression from further developing read modalities, to applying them to experimental write modalities, to finally applying both in the clinical realm. Further research will uncover more ways in which different patterns of stimulation within a region alter activity within that region, as well as how different patterns may differentially alter local or distal circuits. Precisely altered and balanced perturbations and neural pulse sequences, such as shuffle timings and shift timings, will then be used to determine how their effect can support clinical interventions for neurological and neurodegenerative disorders.

Example Modalities

The following subsections describe individual modalities, which may be used to read, write, or perform both functions as integral part of the FCU/MCP.

Neurotransmitter Level and Chirality Measurement and Control

Neurotransmitters are essential molecules at synapses that regulate brain, muscle and nerve function. The most common neurotransmitters are glutamate, dopamine, acetylcholine, GABA and serotonin. At the cellular level, the FCU/MCP will build on neurotransmitter and receptor activation, because chemical synaptic transmission is one of the primary ways by which neurons communicate with one another.

For instance, ligand-substrate interactions, which are a prerequisite for biochemical reactions that are relevant to cognition, are governed primarily by neurotransmitter molecules and provide an ideal example of the potential to employ FCU/MCP as a feedback-based write modality. These molecules exist in one of two forms, each being a molecular mirror image of the other. Isomer-enantiomer ligands function as lock-and-key allowing neurotransmitters to recognize their complementary receptors and permit excitatory or inhibitory synaptic transmission. Mirror image isomer/enantiomers interact with post-synaptic receptor sites, a process that produced a variety of effects depending on environmental conditions. The specific ligand-substrate characteristics, or lock mechanism, required for neurotransmitter activity, are determined by the unique electron-level interactions between asymmetric molecules. Chiral neurotransmitter molecules are found in S(+) or R(−) isomer-enantiomer conformations and have different effects on neural activity and behavior. For example, the S (+) isomer is several times more potent than its R (−) enantiomer. The S (+) isomer is known to induce euphoria, whereas enantiomer R (−) has been linked to depression. The overall greater potency of the S (+) isomer form in such cases suggests that this form may have a higher potential for deep cranial stimulant actions and neurotransmitter availability in the synapse. This leads to behavioral alterations that are noticeable at the corresponding linguistic level. The correlations between the linguistic output and S (+) isomer and R (−) enantiomer values offer corresponding equivalence of transporter's chemical pathways, allowing correlation with other FCU/MCP's read modalities, such as linguistic analysis.

Recent findings indicate that neurotransmitters can be measured using a Fast scan cyclic voltammetry. Measuring and modulating neurotransmitter levels provides a solid treatment approach for subjects with a variety of disorders. Treatment for regulating neurotransmitter levels is to provide the basic amino acid precursors in order to maintain adequate neurotransmitter levels. In this sense, measuring neurotransmitters and drug treatments provide "read" and "write" modalities respectively for analyzing FCU.

Electrochemical Neural Manipulation

Photon-driven conformational changes in protein neurotransmitters form one of the primary mechanisms by which information is transferred and stored within the brain. Apart from controlling the concentration and neural regions affected by controlled neurotransmitter release or inhibition, electromagnetic radiation can be used to a similar effect, by inducing conformational changes in the proteins already present near the synapse site of neurons.

A powerful write modality can be built using FCU-based mechanism for exchanging information within the brain: endogenous photon-triggered neuropsin transduction, followed by conformational changes in protein neurotransmitters. By mimicking the causal process by which the brain writes new information to neural networks, FCU/MCP can co-opt existing chemical processes to achieve control over this activity.

In a neuropsin-mediated unary-coded photonic signaling scheme, neuropsin plays a role of a unary +/− encoder, capable of producing patterns of LTP in synaptic ensembles, and wiring changes in local synaptic circuits. Both phenomena may be reflective of, and serve as a coded reporter of, each of neuropsin's two stable conformational states: i.e., incremental unary (+/−) switches based on value structure of a non-deterministic state, with or without linear or potential pathway. The incremental unary "+" switch is near UV photon absorption by neuropsin, producing its incremental unary "+" state which is G-protein activation. The incremental unary "−" switch is blue (~470 nm) photon absorption, which converts into the conformation incapable of G-protein activation.

Multiphoton absorption by neuropsin may be possible, if neuropsin is in close proximity to a photon source, therefore free radical reactions can generate photons of longer wavelength, >600 nm. Multiphoton absorption of two or more of such (red) photons can provide energy equivalent to that of a single UV photon; this means that if two red photon absorptions occur, it may also serve as the incremental unary "+" switch, substituting for a single UV photon. An advantage of longer wavelength photons is that they travel longer distances in brain tissue than do UV photons.

Other key regulatory enzymes, like NADPH oxidases (NOXs), may be used to create such incremental unary switches. Flavoproteins like NOXs absorb blue photons, which cause them to emit green photons. Like NAD(P)H, ifs autofluorescent, but is higher on the wavelength spectrum. The photons which NOXs absorb are the same photons that the UV-stimulated NAD(P)H emits: ~470 nm (blue). These photons trigger the production of photons of even longer wavelength, by NOXs' well-documented ability to autofluoresce: 520 nm green photons are emitted.

Quantally controlled, unary incremental switches in the brain may use a multiplicity of other (+/−) switches in the brain, as NOX's photonic (+/−) unary coding may serve as switches for yet another regulatory process, such as reactive free radical generation, which produces UV photons that start the scheme, involving NADH, neuropsin in the first place. Therefore, NOX can complete the photonic scheme of the brain's infinite "do loop", reaching quantum tunneling & entanglement, which open the door for long-distance signaling, even from outside the brain.

Downstream consequences of neuropsin's ability to produce spatio-temporal distribution patterns of "+" and "−" states in synaptic domains are potentially profound, in their implications for memory formation, both short- and long-term, each of which are semi-independent processes.

Long Term:

There exists a link between long-term memory (LM) and cellular/synaptic processes such as long-term potentiation/depression (LTP/LTD). Furthermore, LTP/LTD requires some sort of structural changes/protein synthesis:
1. changing neurotransmitter receptor expression,
2. increasing synapse size,
3. changing synapse anchoring, that makes ADP/ATP, being the major energy source in neurons and glial cells, required for LM.

Short Term:

There is good evidence that persistent neuronal firing of those populations of neurons that encode the memory is required, similarly to refreshing computer's rapid-access memory. Apart from ATP/ADP fuelling persistent activity by driving ATP/ADP dependent ionic pumps and the maintenance of synaptic receptors, ATP/ADP has also been linked directly to the emergence of persistent activity through its modulation of ATP modulated potassium channels.

Since the discovery of purinergic signalling the involvement of ATP/ADP-mediated signalling through neuronal and glial receptors is seen in almost every aspect of brain function. FCU/MCP, can guide purinergic signalling, including its effects on learning and memory, focused more on the therapeutic potential of purinergic modulation in various CNS disorders.

Linguistic Analysis

The FCU/MCP approach is based on the concept that cognition, or thoughts, are composed of similar units. Within the brain, thought can be measured, or quantified, based on brain locality, the amount and source of neurotransmitters and other intervening chemicals, as well as pre-existing conditions in the brain that might cause different responses to the same neural stimuli. Outside the brain, linguistic and behavioral patterns can be observed that can be causally traced to these lower-level processes. Because of this fundamental linkage, FCU consists not of just one of these metrics, but is instead a relational quantifier for all of them, and each such unit must account for the various sources of conscious thought. For example, reasoning calls upon events in both long and short-term memory, in addition to applicable learned concepts. Information regarding each of these may appear based on its manifestation to be retrieved, stored and modified differently within the brain, but at the most basic, indivisible level, this information is composed of similarly formatted units.

We can think of language as a function that maps those chemical and cellular processes within the brain to some meaningful expression. To a lesser degree, behavior also fits this definition. Because language is inextricably bound to processes inside the brain, it is a valuable window with which to examine the inner workings of the brain, which is why FCU/MCP's read modalities include linguistic analysis, to map the processes that ultimately lead individuals to express specific behaviors or linguistic expressions.

Linguistic processing is primarily viewed as a read modality, analyzing spoken or written discourse. However, one can also envision applications which in the short term, may propose the use of specific concepts and language constructs in communications with a patient, and in the long term, using language in write modality capacity by the FCU/MCP device capable of automated cognitive therapy.

Functional Magnetic Resonance Imaging (fMRI)

Conventional neurofeedback "read" modality techniques such as electroencephalography (EEG) provide signals that are too noisy and poorly localizable. An improvement in the imaging signal is offered by fast and localizable source signal provided by real-time functional magnetic resonance imaging (fMRI). The temporal resolution of fMRI is in the scale of seconds or less while the spatial resolution is in the scale of millimeters. It has been shown that healthy individuals can use fMRI to learn to control activity in their brain. Recent research has shown that patients with pain disorders can control brain areas involved in pain perception using fMRI-neurofeedback. This self-regulation of brain activity is brought about in the following manner: The subject is in the MR scanner visualizing a signal during which fMRI imaging is performed which is the "read" modality. During the "write" modality, the neurofeedback signal is computationally adjusted. The subject visualizes neuro signal changes in brain regions which is fed back into the signal the subject views.

Visual perceptual learning (VPL) in the early visual cortex of adult primates is sufficiently malleable that fMRI feedback can influence the acquisition of new information and skills when applied to the correct region of the brain. Second, these methods can induce not only the acquisition of new skills and on formation but can aid in the recovery of neurological connections that have been damaged by accident or disease. For instance, a trauma victim suffering from language skill loss can potentially recover those skills through fMRI neurofeedback induction. The structure of thought is that the FCU, which we seek in cognition, must be based on some finite number of neurological connections. These same connections are influenced by the activity of fMRI neurofeedback. This process does not target a single neuron, but a locality of connected neurons, and based on its positive effects on the conscious process of VPL, the FCU represents that reality. In addition, fMRI induction research can provide powerful evidence for the composition of thought because it can be used to determine the minimum amount of neuronal connectivity for the formation of thoughts.

Electroencephalography (EEG)

Techniques such as fMRI are used to detect brain activity, however, the temporal resolution presently available is not good enough for determining unitary math at the cellular level. For this purpose we propose that electroencephalography (EEG) can be used. EEG has better temporal resolution (milliseconds vs. seconds and minutes of fMRI) and it is non-invasive. EEG can be used as a "read" modality to allow measurement of FCU at the cellular level.

EEG allows recording electrical activity in the brain from neurons that emit distinct patterns of rhythmic electrical activity. The aggregate of synchronous neural activity from a large group of neurons emit rhythmics patterns. Different EEG rhythms are associated with normal or abnormal brain activity. There are seven unique frequencies of brain waves (from low to high): delta, theta, alpha, beta, gamma. Each set of frequencies is associated with a brain state such as alertness, sleep, working memory etc.

Conventional EEG tends to have excellent temporal resolution, but it is the poor spatial resolution that makes it difficult to localize important brain activity. High resolution EEG (HREEG) is also a non-invasive technique used to evaluate brain activity based on scalp potential measurements. HREEG is used to enhance spatial resolution over regular EEG by overcoming the head volume conductor effect. One type of HREEG is cortical potential imaging (CPI). CPI allows passive conducting components of the head to deconvolve scalp potential. This powerful spatiotemporal EEG "read" modality will allow to record localized and stimulus specific brain activity.

Transcranial Magnetic Stimulation (TMS)

TMS is another non-invasive technique that can cause neurons to become activated by depolarization or silenced by hyperpolarization. TMS utilizes electromagnetic induction that results in generating electric currents using a magnetic field resulting in activation in a specific brain areas. TMS can be used as a diagnostic tool or for therapy. TMS has been used for the treatment of depression and schizophrenia among others.

TMS can be used as a "write" modality to feedback activation of neurons that require an increase in excitability or silence neurons that are hyperexcitable.

Deep Brain Stimulation (DBS)

Deep brain stimulation, or DBS, is a surgical treatment that requires the implantation of a brain pacemaker that sends electrical activity to specific brain regions. DBS has most commonly been used in the treatment of Parkinson's disease, other movement disorders, depression and chronic pain. Unlike brain lesioning methods of neurological treatment, DBS treatment is reversible.

DBS is primarily useful as a "write" modality for the treatment of chronic diseases such as movement disorders, as it is an invasive technique. The method by which DBS affects neural activity and neurotransmitters is still largely unknown, but it produces high frequency electrical stimulation that reduces neurological disease symptomatology. In some cases, DBS activates ATP release that acts on adenosine receptors and inhibits neural activity therefore mimicking a lesioning effect.

Audiovisual Stimulation (AV)

Audio-visual sources can be used as a neurostimulation input used during neurofeedback. Audio inputs produce signals through the auditory neural pathway for perception of sounds and visual neural inputs activate the visual pathway for perception of light. When audio-visual input is presented to individuals, the correlated brain activity can be measured by the above described techniques. Once the neural activity is measured, inputs are processed into a "writeable" form that is fed back into the audio-visual program.

Ultrasound (USN)

Ultrasound (USN) has recently been shown to non-invasively stimulate brain activity. USN has the capability to increase or decrease neuronal activity, thus making it an ideal candidate for novel neurofeedback applications. One kind of USN is the transcranial pulse ultrasound that has the key advantage of spatial resolution of a few millimeters. Transcranial ultrasound has been shown to disrupt seizure activity in a mouse model of epilepsy. Recent technological advances now allow transmitting and focusing of USN through the intact human skull using an array of phase-corrected ultrasonic transducers placed on the cranium. Such non-invasive, focused ultrasonic intervention permits thermal (high power) and non-thermal (low-power) modes. Non-invasive, thermal ablation of thalamic nuclei using USN has recently been demonstrated to be effective in the treatment of neuropathic pain patients, and promises applicability in non-thermal stimulation and suppression of neural activity.

Motion Tracking/Gait Analysis

The vestibular system, which is located primarily in the mesencephalon and receives input from proprioception receptors from throughout the body, is another promising perspective from which to assess brain function relative to protein folding and misfolding. Since it is integrated with input from the cerebellum, semicircular canals and visual and auditory system and relays information and coordinates the motor system to maintain balance, the vestibular system is responsible for maintaining motion equilibrium. Since this system serves keep the body sensitive to perturbations in the surrounding environment, neurogenic disorders affecting this system are largely marked by motion aberrations that can be detected by multiple body sensors, creating another rich read modality.

Analytical Methods

Brownian Motion Based Analysis

The analytical component of FCU/MCP's will also be based in part on the phenomenon of Brownian motion in order to probabilistically analyze the effect of environmental factors such as electrical charge, the presence of other reactive neurochemicals, and ambient electromagnetic energy. Brownian motion measures particle displacement as proportional to the square root of time elapsed. That is, measuring from a hypothetical time $t_0=0$, displacement d of some Brownian particle will increase in proportion to $\sqrt{t}$ rather than t due to the random forces acting upon the particle. Modeling the impact of many random forces that tend to cancel one another's influence (but not always) is significant to the FCU for a number of reasons. First, the conformational changes in the fluoroproteins that drive the neurochemical element of the FCU must account for some degree of randomness in the incidence of UV energy causing those conformational changes, as well as the chemical energy that is released when they occur. Whereas Brownian motion is used as a stochastic predictive model to describe and account for the uncertainty inherent in particle motion when numerous fast-moving particles interact with one another without any kinetic coherence, the process can be applied to protein-driven neurotransmission as well.

In Brownian motion, a set of particles is described with a series of properties affecting the outcome, such as mass, direction, speed, and interactions with other particles. Over the set of all particles, these factors appear to cancel one another out instead of contributing to a general pattern of motion, as may appear when water travels in one direction (such as in the direction of gravity). In human cognition, we can substitute these attributes for what is observable within the human brain. For instance, instead of describing the motion of particles in a fluid, we can use a similar model to describe the state of protein receptors located on neurons in a specific brain region. Instead of identifying a pattern of motion versus a random state, our approach searches for a pattern of cognitive process versus the absence of such a pattern, as might occur when comparing neurochemical patterns from healthy patients and those with cognitive impairments.

In sum, the greatest applicability of Brownian motion and other stochastic mathematical models to the FCU is the ability to measure "background noise," and to identify some threshold at which a series of neurons is producing such noise or producing an information-rich signal.

Linguistic Axiological Input/Output (LXIO) Analysis

The LXIO (Linguistic Axiological Input/Output) System, developed by Howard and Guidere (2012), is an existing computational analysis suite for evaluating mind state according to observable cues, such as spoken and written language, that is based on unary mathematical principles. This system forms an integral component of MCP by expressing cognitive states in terms of axiology, or the common unary values associated with certain general concepts, such success and failure. Axiological elements such as conception, perception, and intention are taken into consideration. The overall LXIO framework consists of multiple modules, each of which retrieves, parses or processes patient discourse and/or writing. The framework for our analytics engine consists of multiple modules responsible for coherently and systematically retrieving, parsing and processing a patient's discourse. The LXIO modality consists of a computational method that can analyze with numerous processes simultaneously, and is based on the mind-state indicator (MSI) algorithm. The MSI algorithm was developed to explain mental processes that underlie human speech and writing in order to predict states of mind and cognition. The MSI algorithm is covered in patent application Ser. No. 13/083,352, "Method for Cognitive Computing".

The MSI algorithm can detect mood states in individuals by evaluating word value information from their speech based on cultural and linguistic norms. Speech information is derived from concepts such as semantic primitives, which tend to have universal conceptual value. Death, for instance, has a generally negative value across cultures and languages, whereas concepts such as rest and happiness have positive values. MSI takes into account both the content and the context (vocal, body and semantic) in each conceptual primitive. That means both a comparison of words to known values and expressions to known mind states, such as consistent body language (folding arms, touching face etc.) or vocal tonality (pitch variations correlated with levels of expressiveness, as well as volume and word emphasis).

Markov Decision Process (MDP)

Viewing cognition as a mapping of one set of phenomena to another, it is easy to over-emphasize its spatial components at the expense of its temporal construct. Since cognition is a dynamic process heavily dependent on the environment, the units we use to describe and interpret thought must reflect its temporality. FCU/MCP uses the concept of mind state, or an approximation of the human mind or some subset of it at any point in time. Mapping the temporality of thought requires the connection of several such mind states over time, which are themselves composed of FCU units. In order to develop the relationship between the FCU and temporality, FCU/MCP uses the Markov Decision Process model to build mind state transitions through reasoning and decision-making. This analytical process forms the foundation for the two linked goals of FCU/MCP: the empirical and predictive analysis of cognitive information, as well as the modification of brain processes to alter that information.

Cognitive processes depend on their current state. That is, information from the past, if not already contained in the process's current state, will not contribute to greater precision or informational clarity of the process. For that reason, we use as the basis of our analysis a process flow model known as the Markov chain, which is the building block of the Markov Decision Process (MDP). The MDP is unique in its ability to allow decision makers to evaluate and act on incomplete information, or in the presence of some uncertainty.

Since states of mind evolve and change over time, then each change has probabilistic characteristics that can be placed at various points on a one-dimensional spectrum between explicitly positive or explicitly negative. Based on this probabilistic property of mind state transitions, there is also a range of therapeutic, or manipulative, interventions that depend on that probability. The means by which we measure the efficacy of such treatment is based on the responses of the patient throughout treatment and/or experimentation, and the positive or negative values which those responses connote.

We can describe this process in a straightforward manner. When in some mind state s, there is some probability p, where $0<p<1$, that the subject will shift to a new mind state, s', with some benefit b. Markov chains, in our application, consist of a series of such shifts. The process of thought can be thought of as a sequence of some number of distinct states over a period of time, and the process can be modeled based on the probability of transition from one state to the next. These transition probabilities depend on n previous states and nothing more. For our purposes, n is generally set to 1 in order to bound our analysis to the current state and its successor.

For example, if we have a MDP for some four different mind states $\{S0, S1, S2, S4\}$, from each mind state there is a possibility of choosing an action from the set $\{a0, a1 \ldots an\}$. When that action is chosen and executed, the subject assumes the successive mind state. Thus we have two components: potential decision (the choice of an action in a given state), and transition probabilities for each decision node. Finally, these transitions can generate rewards based on the positivity or negativity of the resulting mind state.

In order to fully and effectively map mind states to probabilistic transitions, it is important to develop a submodel that accounts for processes within the brain, such as the activation of specific neurons or neural networks in response to chemical stimuli. To this end, an algebraic component can be introduced in order to account for increasingly numerous concept and brain region activations. Beginning with an set S (infinite for our purposes here) representing brain regions that are candidates for activation, a σ-algebra A on that set can be then introduced, with elements a⊆A known as activation sets. Note that by definition, a⊆S. Another set W is then introduced, with elements as labeled concepts in the brain that correspond to conceptual constructs. For some subset of A there exists a mapping P: a∈A→w∈W, or the concept activation mapping. The elements of this subset are action potentials. Thus, there is some mapping P: □W→ã□Ã be a mapping we call the brain activation mapping. From this mapping, we can determine the probability of state transitions because brain region activation/inactivation is the most immediate cause of mind state change. If μ is some measure on S, then F:A→{+,−} is a parity mapping. An axiology, which we use to link linguistic information to brain region activation information in our FCU analysis, is a mapping Ξ: W→{+,−} generated by computing $f(w) =_a F(s)^{d(\mu)}$ with a=P(w). We then project Ξ(w)=sig(n(f)) for the final result.

Using this system, we can interpret data relating to the mind state of a subject by examining the mind's abstract structures: axiological concepts expressed in language, as well as periods of brain region activity and inactivity. These structures are populated by information from present read modalities, ranging from simple observation to biopsy and long-term analysis. Throughout the brain there are various forms of activations (electrical, chemical, biological) each contributes individually or within groups to the formation of new concepts, which define a positive or negative mental state.

Maximum Entropy (Maxent) Statistical Model

The Maximum Entropy (Maxent) statistical model is of high significance to the FCU/MCP. The Maxent Model is a method of estimating conditional probability. In the case of FCU/MCP, the core equation can be used, H(p)=−Σ~p(x)p(y|x)log p(y|x), as a component of both the read and write modality because each of these is influenced by probabilistic events.

Given the expanded Maximum Entropy equation:

$$L_{\tilde{p}}(p) \equiv \log \prod_{x,y} p(y|x)\tilde{p}(x,y) = \sum_{x,y} \tilde{p}(x,y) \log p(y|x)$$

The following data is obtained:
X: input value (can consist of any elements which can influence the results; also note that x is a member in the set of X.)
Y: output value; note that y is a member in the set of Y.
P (y|x): entire distribution of conditional probability
~p(x,y): empirical probability distribution
~p(x,y)=1/N*number of times that the pair (x,y) occurs in the sample
f(x,y): The expected value of f with respect to the empirical distribution ~p(x,y) is precisely the statistic we use to measure probability of state transition and activation probability. This gives us ~p(f)=Σ~p(x)p(y|x)f(x,y). Solving for p(f)=~p(f) then yields Σ~p(x)p(y|x)f(x,y)=Σ~p(x,y)f(x,y).

In natural language processing (NLP), Maxent essentially means assigning a probability to each possible meaning of a given word that is being processed. For instance, in the English language the word produce can have at least two meanings: as a verb, it means to generate or create (meaning 1), and as a noun it generally refers to agricultural harvest and output (meaning 2). If we assume that these are the only nontrivial uses of the word, then p(Meaning 1)+p(Meaning 2)=1. While this is a highly simplified example that does not address the probability distributions within each meaning (such as the fact that it is much more likely to be used in the verb form), it does provide a basic framework that can be expanded to account for increasingly complex linguistic constructs.

A stochastic model is a model that represents the behavior of the seemingly random process of NLP when fed unstructured information. They employ a series of five templates, and construct probability distributions for each of them by employing constraints based on context, source language and destination language. For instance, "template 1" has contains the loosest set of constraints, since a distinct target language is not specified and there is likely no morphological change. However, templates 2-5 perform translation based on syntactic context, verb proximity, and verb character. A stochastic model's relevance to FCU/MCP is its distinction between probability and determinism in conceptual constructs. In an ideal setting, FCU-based analysis links each unit to another one intuitively, and there is very little (if any) uncertainty that the FCU that maps to processes within the brain accurately reflects those processes. Here, the model is much less certain and must account for the idiomatic differences between languages. While FCU as a theoretical method does not face this problem because linguistics are simply an outer layer of a much deeper series of cognitive activities, imperfections in data gathering may provide a viable application for such a model in our research. For instance, garbled speech (thanks to recording hardware, data corruption, or human error) may create a set of unknown and known words in a single sentence, and the context of the known words must be used to create a Maxent model for the potential unknown word matches.

Another possible use of a Maxent model is predictive analysis. Given a mind state correlated with a series of spoken concepts, future behavior (depressive vs. non-depressive) and linguistics (attributable to cognitive state) can be discerned to a reasonable measure of certainty using Maxent. In the context of MCP, a number of contextual templates could be designed based on variables such as mind state (+/−), or temporality (i.e., whether the concepts discussed refer to past or future events). This is because multiple concepts that occur in the same temporal frame are likely to be related.

From the above research we can discern a number of Maxent uses within the FCU/MCP. The first is the use of statistical methods to determine the most likely intended conceptual meaning of homophones such as produce, or rose. Researchers previously applied Maxent to sentence content, meaning that the Maxent solution to a sentence containing rose would vary based on the presence or absence of other concept words such as flower, petal, or red in the first meaning or seats, standing, or seated in the second meaning. FCU would apply maxent in a similar manner, but would consider input from a multitude of sources. For instance, the presence of hand gestures associated with certain activities, such as rising from one's seat, would figure in the FCU-based read modality analysis of a sentence containing rose. In addition, the normalized mind state associated with flower(s), if significantly different from background, would also contribute to the final determination of the word's meaning and consequent connection with conceptually and semantically adjacent words and ideas.

Maxent can also be applied to mind-state and linguistic tendencies of individuals and sets of individuals who share some cognitive similarity, such as Post-traumatic stress, Parkinson's disease, or Alzheimer's disease.

A template-based Maxent model algorithm for predictive read modality analysis might look like this:

Process_1 (string s, concept set S)
  Given SENTENCE
    Get WORD COUNT
  If s(0), s(1) belong to concept, merge(s(0),s(1))
  else remove(s(1), s)
    process(string s, concept set S)
Process_2(concept set S)
  FOR each concept in S
    Get temporality
    Get mind state
    Get set of possibly related concepts in order of probability This presents just one simple template based on temporality and mind state, two factors which we know will affect the physical execution of cognition within the brain based on chemical activation and/or brain region activation. Maxent can be applied to determine the probability that a given neural network will be activated at certain combinations of temporality and mind state, but that will likely require significant data gathering on the individual beforehand.

Example Embodiment

An embodiment of the invention can be described as follows: (1) one or more Sensors each implementing at least one read modality, (2) an Analyzer comprised of commodity hardware parts, whose primary purpose is to provide data look-ups in a pre-loaded database containing FCU templates for different read and write modalities, and perform FCU computations on them, recognizing patterns provided in input, and create therapeutic signal pattern, and (3) one or more Effectors, reconfigurable at runtime to efficiently deliver signal sequences.

The Analyzer is connected via Interface 1 to an array of Sensors. The Sensors are used to perform functions like examining areas of brain tissues, collect the frequencies of neuronal activity, or aggregate linguistic and behavioral information of the patient, and transmit them to the Analyzer for processing.

Interface 2 connects the Analyzer to one or more Effectors used to stimulate targeted neural tissue, in order to induce and guide brain activity. The Effectors are devices that can deliver signal to the targeted neural tissue via invasive (e.g., implanted optical probes) or non-invasive methods (e.g., transcranial stimulation).

The Analyzer, via Interface 2, controls the Effectors to induce neuronal activity feedback, which is collected via Sensors from Interface 1 as a series of action potential spikes or linguistic patterns, ultimately represented as a stream of unitary system values. The Analyzer, using this input, isolates a set of FCU templates, such as the baseband oscillation frequencies specific to the area of activity, and matches them to a set of unitary system signals which can be delivered via a write modality, to induce electro-chemical release sequences, in turn triggering specific protein switching/folding sequences in the cells.

The Analyzer, via Interface 2, dynamically reconfigures the Effector to produce the required sequences of signals, which are delivered to the brain. The signals activate changes such as the release of a specific set of positive (+) or negative (−) optical isomers of chemicals in the tissue. The chemical communications triggered by the isomer release activates tissue changes in the targeted area.

To better understand the embodiment, below is an example of FCU/MCP device used for treatment of Alzheimer's disease symptomatics:

In the case of Alzheimer's disease, the device would use several read modalities collected using a Multi-modal Body Sensor Network (mBSN), such as Howard and Bergmann (2012), consisting of multiple sensor types: an Integrated Clothing Sensor System (ICSS) to measure knee joint stability and arm trajectory, and a vocal data collector linked to the linguistic analysis engine to detect and analyze mind states and temporal delays based on spoken language. Analyzing movements of both the upper and lower limbs provides empirical evidence regarding mind state (e.g., as a proxy for uncertainty), which can be coupled to linguistic and behavioral output for a richer diagnostic picture of early Alzheimer's patients. Motion information from patients that are likely to develop Alzheimer's disease is collected in terms of (+) and (−) terms: involuntary movements, like in Myoclonus, that are sudden and brief, can be classified as (+) or (−). (+) movements are caused by sudden muscle contractions, while (−) movements are caused by sudden loss of muscle contractions. Similarly, mind state information collected is in the form of +/− connotations to words suggesting +/− mind states. Data collected from Sensors are then sent via Interface 1 to the Analyzer.

In the Analyzer, using stored FCU models, computes these unitary values of +/− and also computes the treatment strategy. The treatment strategy is delivered into Effector through Interface 2, which in this case implements the Ultrasound modality, which in turn delivers drugs to treat Alzheimer's symptomatology. In the case of Alzheimer's disease, the FCU model computes delivery of +/− isomers of anticholinesterase, the drug commonly used to treat Alzheimer's disease but is typically given intravenously. The novelty of this treatment strategy is using FCU to deliver the drug by 1) choosing enantioselective (+/−) versions of anticholinesterase for drug delivery, 2) using the "write" modality of Ultrasound to deliver in a more precise manner the drug directly to neurons affected by Alzheimer's. The manner in which this would work is as follows: ultrasound beam targets the hippocampus, which is heavily implicated in controlling memory and is affected by early Alzheimer's disease. The ultrasound beam opens up a temporary drug delivery passage in the blood brain barrier with the help of microscopic bubbles in intravenously injected that travel to brain capillaries. There are several anticholinesterases, such as phenserine and rivastigmine both of which have enantiomers. Phenserine in addition to inhibiting cholinesterases, is able to modulate beta-amyloid precursor protein (APP) levels. Interestingly, phenserine has differing actions of its enantiomers: (−)-phenserine is the active enantiomer cholinesterase inhibition, while (+)-phenserine, also known as posiphen has weak activity as an cholinesterase inhibitor and can be given at high concentrations. It is important to note for Alzheimer's treatment that both enantiomers are equipotent in reducing APP levels.

In order to treat Alzheimer's disease symptomatology based on FCU, the Analyzer selects the best fit enantiomer of anticholinesterase and utilize (+)-posiphen, either alone or in combination with (−)-phenserine delivered directly into the hippocampus attenuate the progression of Alzheimer's disease at an early stage. In this manner of treatment, memories stored in the hippocampus will not be lost.

Applications of Invention
Early Diagnosis of Neurodegenerative Disorders

The effects of neurodegenerative disorders such as Parkinson's disease and Alzheimer's disease can ultimately be alleviated, or at least minimized, by the development of an accurate, non-invasive early detection mechanism complementary to that of linguistic analysis that is based on behavioral trends over time. Thus, part of FCU/MCP development will include current research and expand on recent findings by validating a non-invasive diagnostic methodology for the early detection of Parkinson's disease. Specifically, the integration of body sensor networks will provide a physical dimension to FCU/MCP's read modality. Multimodal Body Sensor Networks (mBSN) consist of multiple sensor types: an Integrated Clothing Sensor System (ICSS) to measure knee joint stability and arm trajectory, and in the future a vocal data collector linked to the LXIO analysis engine to detect and analyze mind states and temporal delays based on spoken language.

By focusing our efforts towards early detection of changes in global cognitive and postural functioning during everyday life, our research promises to provide a direct match with the symptoms that define this disease. The mBSN approach to early detection is especially effective and appropriate in cases where patient risk is too low to warrant surgical intervention, but where a patient nevertheless requires some level of clinical care or observation. In these cases, write modalities could simplify the patient's choice about whether to treat a given disorder based on the low complication risk owing to the precision of FCU/MCP write modalities.

Body Sensor Networks (BSN) offer a new way to collect data during the performance of everyday tasks involving physical movements. Body Sensor Network data for broad categories of activity, including standing, walking, and repetitive tasks that will enable rapid subject dataset growth, will be used to measure values linked to the onset of neurodegenerative diseases, such as joint instability and erratic arm trajectories. Analyzing movements of both the upper and lower limbs offers the chance to collect empirical evidence regarding mind state, which can be coupled to linguistic and behavioral output for a richer diagnostic picture of the subject.

Alzheimer's Disease

The well-known chemical symptoms of neurological disorders such as Alzheimer's disease often manifest themselves too late for treatment to sufficiently slow or reverse the onset of the disorder. The current research emphasis on early detection, preventive lifestyle adjustment, and pharmaceutical intervention presupposes that noninvasive methods either will not work, or that doctors are simply unable to detect the disease in time to effectively apply those treatments. To this end, FCU/MCP system seeks to apply methods of improved early detection in order to more effectively apply "write modalities" such as the introduction of chemical inhibitors of the beta-amyloid proteins that build up within the brain and cause Alzheimer's disease.

We can use a similar model to introduce constraints on the brain regions we measure. In patients with Alzheimer's disease, increased presence of hyperphosphorylated tau protein aggregates and amyloid senile plaques are telltale neurobiological signs of the disorder. We know the effect of tau proteins and plaques at the individual neuronal level, and thus can extrapolate those effects so that they match what is observed in patients with Alzheimer's. Because their cognitive faculties appear less orderly than those of healthy patients, dementia patients tend to exhibit more neurological chaos, or randomness, that doesn't contribute to coherent thought or linguistic output. FCU/MCP device can apply Brownian motion analysis to the affected brain regions, neural networks, and individual neurons, and use this method to predict the coherence of a patient's mind state. This may in turn help us to better define the thresholds at which certain types of cognitive tasks, such as memory recall and language processing, begin to be affected by dementia onset, and the tolerance of healthy cognition for such levels of random activity in the brain.

For disorders such as Alzheimer's disease, symptoms of the disease include cognitive deficiency and memory loss; biomarkers include indicators found in cerebrospinal fluid, as well as genetic factors and the presence of abnormal levels of beta-amyloid proteins in the brain. However, a true "read modality" cannot be limited to symptomatic analysis based on these factors alone.

The approach is based on using the Fundamental Code Unit (FCU) to perform pattern recognition tasks on the linguistic and behavioral data emerging from observations of a patient. Data streams can be as unobtrusive as recording a spoken interview or observing changes in gait over several years' time, and as invasive as collecting cerebrospinal fluid. Data from each of these acquisition methodologies are then incorporated into the FCU template. While FCU is a brain language of sorts, it is fundamentally different from spoken languages in two ways. First, languages such as English map spoken words (utterances) and/or written (pictorial) representations to cognitive constructs; translators then draw equivalencies between English and other languages. The FCU incorporates characteristics of both. It is similar to a "language" of cognition because it is applicable to all intelligent, brain-based entities. It is similar to a translator because it draws the same type of equivalencies between molecular processes, such as an increase in beta-amyloid proteins, and physically observable processes, such as uncertain gait and slurred language.

The FCU/MCP's selection of write modalities depends largely on the biomarkers present and the progression of the disorder that is detected. For instance, an ideal treatment for Alzheimer's disease would both slow the BA protein buildup in the brain and reverse the cognitive effects that have already begun to appear. In the absence of a clinical treatment to reverse the effect of beta-amyloid protein buildup in the brain, early detection of Alzheimer's disease is the most popular management regime.

For the latter component of the treatment, a "write modality" for Alzheimer's disease is necessary that will reconstruct the connections between neurons that provided the basis for now-missing memories. In order for this to be possible, some means of relating missing neural information to what is readily available is needed. The FCU can contribute to symptomatic (and causal factor) reversal by reconstructing partial neural connections from extrapolation of incomplete FCU data, combined with linguistic and behavioral data streams. While the clinical technology does not yet exist to apply these innovations to patients, a robust means for both cataloging and relating different neural data streams, or FCU, is a necessary prerequisite.

Parkinson's Disease

Mental states are the manifestations of particular neural patterns firing and neurotransmitters exchanged between neurons. These states have neural correlations corresponding to specific electrical circuits. A decade ago there was a deep interest in functional neurosurgery for neural disorders, such as movement disorders as well as neurodegenerative cognitive impairment. This led to an increase in our understanding of the underlying neural mechanisms and circuitry involved in basal ganglia disorders with improved surgical techniques and the development of deep brain stimulation (DBS) technology, which paved the way for major advances in the treatment of Parkinson's Disease (PD) and other neurological disorders.

To better understand the role of the posterior parietal cortex, basal ganglia and cerebellum in the control of movement, researchers inserted electrodes into patients with movement disorders such as Parkinson's disease (PD). These electrodes helped stimulate the control network system (CNS) for which low frequency (4-15 Hz) field potentials were recorded that correlated with the patient's involuntary movements. Interestingly, recent studies have discovered that the pedunculopontine nucleus (PPN) in the upper brainstem has extensive connections with several motor centers in the CNS and is very important in controlling proximal muscles for posture and locomotion.

This area is over-inhibited in many patients, which is a major cause of their inability to move, i.e. in an akinesia state. This inhibition can be overcome by stimulating the PPN directly and can thus return previously chair-bound patients to a useful life. That is why, Deep Brain Stimulation (DBS) of the pedunculopontine nucleus (PPN) is a novel neurosurgical therapy developed to address symptoms of gait freezing and postural instability in Parkinson's disease and related disorders.

FCU/MCP based diagnosis will offer improved and early detection of PD symptoms and provide effective treatment strategies. Similar to Alzheimer's patients, but more importantly for a movement disorder such as Parkinson's, motion information can be collected from Sensors such as body sensor networks (mBSN) (Refer to FIGS. 5, 6). Motion data is collected from patients that are likely to develop Parkinson' disease is collected in terms of unary (+) and (−) terms: involuntary movements, like in Myoclonus, that are sudden and brief, can be classified as (+) or (−). (+) movements are caused by sudden muscle contractions, while (−) movements are caused by sudden loss of muscle contractions. This information is sent to the FCU based Analyzer that computes unary treatment strategies based on unary biomarkers of Parkinsonian movement symptoms. Again, similar to Alzheimer's ultrasound can be used a write modality to deliver drugs into PD associated brain regions delivering enantioselective phenserine and posiphen (same drugs can be used for both AD and PD).

Pain Detection and Management

Chronic pain affects approximately 25% of the U.S. population. Chronic pain is classifiable according to two types: neuropathic pain and nociceptive pain. Neuropathic pain is caused by damage to the nervous system, and is described as a "burning, tingling, shooting or lightning-like" pain. Examples include neuralgia, complex regional pain syndrome, arachnoiditis and postlaminectomy pain, which is residual pain following anatomically successful spine surgery and a common indication for neurostimulation therapy. Compared to nociceptive pain, neuropathic pain is more severe, more likely to be chronic, and less responsive to analgesic drugs and other conventional medical management.

Nociceptive pain originates from disease or tissue damage outside the nervous system, and it can be dull, aching, throbbing and sometimes sharp. Examples include bone pain, tissue injury, pressure pain and cancer pain. Nociceptive pain is caused most directly by peripheral nerve fiber stimulation, and is classified as such because the causes of nociceptive pain generally have at least the potential to harm body tissue.

Current objective diagnostic procedures for chronic pain include imaging techniques such as computed tomography (CT), magnetic resonance imaging (MRI) and intramuscular electromyography (EMG). CT and MRI provides information about anatomic abnormalities, but are expensive and do not give information about pain type or intensity level. EMGs provide objective evidence of nerve dysfunction. However, these strategies are invasive and often painful. Newer objective pain detection methods include, quantitative sudomotor axon reflex test (QSART) and autonomic function "hot/cold" pain detection test. Although these methods are effective in research labs, they are difficult to use in clinical settings, often require special training, and are hard to bill for. What is needed is an objective measure that detects the presence or absence of pain as well as an objective assessment of pain intensity level that the patient is feeling.

Neuropathic pain arises from damaged neural tissues that can be essential when the neural injury is in the brain or spinal cord. In patients with intractable central neuropathic pain the pain seems to be caused by spontaneous oscillations in the 'central pain matrix' which consists of the periaqueductal gray, peri-ventricular gray (PAG/PVG), globus pallidus, thalamus, anterior cingulate, insula and the orbitofrontal cortex. It was found that driving the PAG/PVG by stimulating at 10 Hz, one can eliminate the oscillations and reduce the patients' feelings of pain very considerably. Pain suppression is frequency dependent and pain relief occurred at PVG simulation levels ranging from 5-25 Hz. There are also correlations between thalamic activity and chronic pain. This low frequency potential may provide an objective index for quantifying chronic pain, and may hold further clues to the mechanism of action of PVG stimulation.

While it has been widely discussed that specific frequencies affect neural tissue functioning and development, the mechanisms guiding this effect have not been found. Understanding how frequencies affect the complex electrochemical structures and processes in neural tissue, and being able to determine the ranges and sequences that aid and/or restore normal neural activity, are seen as the next step in addressing neurological disorders. Furthermore, non-neural cells are driven by electrochemical processes and can be subjected to similar treatments.

Current neuropathic pain management strategies either require surgery or pharmacotherapy. Surgical strategies are invasive and often require nerve stimulation or destruction of nerve cells. These invasive techniques often cause even more damage to the nervous system which can enhance the pain level. Additionally, none of the surgical techniques have been found to be uniformly successful in managing neuropathic pain. Pharmacotherapy is not efficacious and could have many side effects. In some cases, multiple drugs are necessary for optimize pain level and insufficient data exists for combination drug therapy for neuropathic pain. Transcranial direct current stimulation (tDCS) or TMS can be used as a write modality. TDCS permits weak current stimulation of specific areas of the brain to increase or decrease brain wave patterns as needed for specific treatments. It has been shown that tDCS and TMS can be used to reduce fibromyalgia pain. In this manner, DBS or HD-EEG can be used as read modality and tDCS or TMS can be used as write modality to both diagnose and manage chronic pain using FCU/MCP.

Deep Cell Stimulation

Cell growth is one of the primary results of the cell cycle, and can be accelerated or slowed by a variety of factors. Growth factors work to promote both cell differentiation and maturation, and these processes can in turn be manipulated to promote or decelerate the growth of cell mass. Many cytokine regulator proteins, for instance, work to increase the growth rate of hematopoietic and immune system cells. Some of these, such as Fas ligands, are used to program cells to destroy themselves at pre planned intervals. Still other growth factors are communicable by ever-circulating proteins suspended in body fluid, and work by binding to surface receptors on the target cell.

In much the same way that neurons can be activated or inactivated by neurotransmitters, cells can self-destruct, accelerate growth, or slow growth based on chemical messengers and growth factors. To harness this ability for scientific or clinical ends requires a thorough understanding of the "language" in which cells communicate with one another hormonally. FCU/MCP provides a framework that can be applied not only to the biology of cognition, but to physiology itself. Specifically, we already know that FCU/MCP can be harnessed in order to manipulate specific neurons and neuron networks by using a read modality to interpret their signals and a write modality to modify them. A very similar methodology can be applied to injury and disease victims by manipulating cell growth to regenerate lost tissue, or restrict the growth of malignant cells. Deep Cell Stimulation (DCeS), along with the diagnosis and treatment of brain disorders, is one of the most promising applications of the FCU/MCP framework since it applies to so many clinical disorders, including osteoporosis, hypohemia, and traumatic injuries such as broken bones and injured skin.

Unique Social and Long Term Consequences of the Invention

FCU represents a potential paradigm shift in Artificial Intelligence, both in its facilitation of cognitive analysis and cognitive manipulation. Apart from the gains to be made by structuring AI to match the physiological and physical attributes of intelligent cognition as we currently know it more closely, there are a number of other potential advances with profound social implications.

By bridging the structural gap between "artificial" and "real" intelligence, the capacity for these intelligences to interact with one another becomes much more realistic. This also means that AI can be used as a cognitive bridge between human intelligences that were previously linked by comparatively crude methods (read: spoken and written language). The development of the FCU on a large scale thus has a number of wide-ranging effects. First is the potential to obviate language. The core of the FCU concept is the notion that, regardless of what happens at the syntactic layer of linguistic output, it can be ultimately traced to physical and biochemical processes within the brain. Since these processes are identical among humans, achieving the ability to read thoughts, emotions, mind states, and intentions at this low level has the potential to change the way humans interact.

If we imagine that the FCU has in fact transformed the way people communicate in this way, there are certain features we can expect to see in society and at the individual level. Psychotherapy will begin to resemble streaming content from Netflix as interfaces develop that can transmit massive amounts of cognitive information with minimal latency. In fact, a "psychologist" may in fact be a synthetic intelligence or network of such entities. Since information sharing in this case would no longer depend on the ambiguities of linguistic idiom, native tongues, or nonverbal expressions. Since specific stimuli (dreams, fantasies, horror, etc.) are composed of the same FCU units as baseline conscious thought, the sensations evoked by each of these could be provided without going to the movies, watching TV, reading or even experiencing the stimuli firsthand.

One of the more disconcerting features of a society such as this one that has transcended the linguistic and cultural differences that language barriers pose is the ability to replicate an entire "brain image;" that is, the sum of an individual's experiences, actions, and memories that contribute to the individual persona. While this may appear positive due to the ability to "back up" a consciousness, the notion that making a full, downloadable copy of a human life begs some serious questions about privacy and individual liberties. For instance, could a person be "copied" unwittingly and have their analytical faculties put to use without their consent? Surely data mining and advertising companies would find ways to exploit this newfound intimacy with the human psyche at the individual level. In 1984, Orwell wrote that even living under the most intellectually and culturally repressive regimes, one still remained the master of what remained inside his/her brain. With the ease of potentially surreptitious access to the brain, even Orwell may have been too optimistic.

On the other hand, the ability to copy and distribute an individual's cognitive identity may allow great strides in therapeutic treatments for neurodegenerative disorders. Diseases such as Alzheimer's, for instance, work by slowly eroding the neural connectivity between brain regions until memories, skills, instincts and other aspects of one's identity bound to their brain matter disappear. If the disease is detected sufficiently early, it may be possible to recover the majority (or even totality) of what is all too often inevitably lost to these diseases. Connections within the brain could then be reconstructed based on clinical researchers' knowledge of the precise mechanisms causing a given neurodegenerative symptom (i.e. a lack of sufficient connectivity between brain region a and brain region b).

Regarding communication itself, knowledge of the FCU can be applied to create and analyze the same cognitive structures that appear in language, such as metaphors, idioms, and figures of speech. However, since the underlying conceptual content is laid bare, the utility of these constructs may decrease, as we are increasingly able to apply the FCU to problems of translation and analysis. Linguistic analysis engines that are FCU-based need not collect data on chemical and physical phenomena within the brain in real time. Instead, a statistical analysis of the FCU's role in phenomena such as anger, depression, and deceit (and the underlying processes that drive them) can be correlated with the audiovisual data available, including speech, mind state, and nonverbal expressions. As more FCU data are collected through thorough experimentation, the analytical engine becomes more accurate, and the ideal of a "universal translator" becomes more realistic.

The ability to copy high-fidelity cognitive engrams has a variety of additional applications relating to the ability to "live" or "re-live" specific experiences, possibly in a manner different than they actually occurred. In the therapeutic realm, sufferers of PTSD and similar disorders may undergo therapy regimes that return them to the traumatic experiences that are the cause of their disorder. In addition, "re-living" experiences may alter the way justice is sought, with witnesses being able to trace specific experiences and examine them with a clarity that may have been lost in a fog of adrenaline and other hormones, especially if the experience was a traumatic or intense one.

The above predictions only presuppose the ability to "read" FCU information from the human brain. The ability to write it inside the human brain may yet be realized, and if it is, the collective notions of individuality, soul and reality will likely be fundamentally altered. The ability to erase memories, create new ones, and essentially construct a human psyche from the ground up (instincts, habits, tendencies, preferences, and even personality traits) may tempt some to attempt creating the "perfect" human, much like the eugenics movement of the early 20$^{th}$ Century. In addition, since cognitive factors such as those listed above are hypothetically alterable, people may elect to have themselves altered in order to conform with standards or expectations set by society at large. In addition, knowing what little we do about the effect of such re-writing on the brain itself, there may be no limit on the number of times a person can be "re-written," and we have no way of knowing at what point a person ceases to assume their former identity and assumes a new one.

Another implication of the ability to "write" to the human brain in the natural FCU language of the brain is to manufacture increasingly accurate predictions of the future. Using the Intention Awareness concept, the ability to acquire FCU information from relevant actors will make models of causality and social activity forecasts significantly more accurate and useful to decision makers.

In a future where neuroscience and AI are largely governed by the discovery of the FCU, we can also expect the emergence of new data storage methodologies, since the FCU is essentially a filesystem for the brain. Data connectivity, as it is today, will still remain an important of the future computational infrastructure, but data storage and transfer will less resemble the transfer of sequences of bits than the exchange of much smaller bits and pieces of data, since the human brain is more capable of extrapolation than current computational hardware/software. Given the right data "seeds," FCU sequences can likely be reproduced without the whole data stream.

What is claimed is:

1. A method for affecting living tissue comprising:
   receiving at least one signal from at least one read modality, the signal representing at least one parameter or measurement of living tissue;
   computing at least one signal to effect alterations to the living tissue based on the received input signal; and
   delivering the at least one computed signal to the living tissue through at least one write modality to effect alterations to the living tissue.

2. The method of claim 1 wherein the at least one read modality comprises: neurotransmitter level and chirality measurement, linguistic analysis, functional magnetic resonance imaging, electroencephalography, deep brain stimulation, audiovisual stimulation, or motion tracking/gait analysis.

3. The method of claim 1 wherein the at least one write modality comprises: protein transduction, electrochemical methods of signaling, neurotransmitter level and chirality regulation, linguistic analysis, transcranial magnetic stimulation, deep brain stimulation, ultrasound signaling, audiovisual stimulation, photonic pathways inside and outside the brain, proton pathways inside and outside the brain.

4. The method of claim 3 wherein the use of photonic pathways inside and outside the brain provides broad regulatory power over neuroplasticity.

5. The method of claim 3 wherein the use of photonic pathways inside and outside the brain provides broad regulatory power over memory function.

6. The method of claim 3 wherein the use of proton pathways inside and outside the brain provides broad regulatory power over neuroplasticity.

7. The method of claim 3 wherein the use of proton pathways inside and outside the brain provides broad regulatory power over memory function.

8. The method of claim 1 wherein the at least one signal is computed using a structural mathematical system.

9. The method of claim 1 wherein the at least one read modality or the at least one write modality comprises ATP and ADP-mediated signaling through neuronal and glial receptors.

10. The method of claim 1 wherein the at least one read modality or the at least one write modality comprises events related to autofluorescence.

11. The method of claim 1 wherein the at least one read modality or the at least one write modality comprises a neuropsin-mediated unary-coded photonic signaling scheme.

12. The method of claim 1 wherein the at least one read modality or the at least one write modality comprises a neuropsin-mediated unary-coded multi-photonic signaling scheme.

13. The method of claim 1 wherein the at least one read modality or the at least one write modality comprises stimulating or decelerating growth of specific cells throughout a body using Deep Cell Stimulation (DCeS).

14. The method of claim 1 wherein the method is used for diagnosis and treatment of neurodegenerative disorders including at least one of Alzheimer's Disease, Parkinson's Disease, and Huntington's Disease, or for diagnosis and treatment of other disorders.

15. The method of claim 1 wherein the method is used for Pain Detection and Pain Management.

16. A method for interpreting brain patterns and structures comprising:
    receiving at least one signal from at least one read modality, the signal representing at least one parameter or measurement of living brain or spinal cord tissue;
    detecting normal and deleterious signaling patterns in brain or spinal cord tissue by analyzing the received at least one signal.

17. The method of claim 16 wherein the method is used for diagnosis and treatment of neurodegenerative disorders including at least one of Alzheimer's Disease, Parkinson's Disease, and Huntington's Disease, or for diagnosis and treatment of other disorders.

18. The method of claim 16 wherein the method is used for Pain Detection and Pain Management.

19. A method for interpreting and manipulating brain signals comprising:
    receiving at least one signal from at least one read modality relating to at least one of a photonic pathway, a proton pathway, an electron pathway, and neural coding and signaling mechanisms, the signal representing at least one parameter or measurement of living brain tissue;
    analyzing the input signal based on a detailed model of signaling pathways inside the brain to generate at least one signal to be delivered to the brain tissue; and
    delivering the at least one signal to the brain tissue using at least one write modality providing broad control over neuroplasticity and memory function.

20. The method of claim 19 wherein the at least one read modality or the at least one write modality comprises ATP and ADP-mediated signaling through neuronal and glial receptors.

* * * * *